(12) United States Patent
Simon et al.

(10) Patent No.: US 11,298,535 B2
(45) Date of Patent: Apr. 12, 2022

(54) NON-INVASIVE VAGUS NERVE STIMULATION

(71) Applicant: ElectroCore, Inc., Basking Ridge, NJ (US)

(72) Inventors: Bruce J. Simon, Mountain Lakes, NJ (US); Joseph P. Errico, Warren, NJ (US); John T. Raffle, Austin, TX (US)

(73) Assignee: ELECTROCORE, INC, Rockaway, NJ (US)

( * ) Notice: Subject to any disclaimer, the term of this patent is extended or adjusted under 35 U.S.C. 154(b) by 0 days.

(21) Appl. No.: 17/220,805

(22) Filed: Apr. 1, 2021

(65) Prior Publication Data
US 2021/0220644 A1 Jul. 22, 2021

Related U.S. Application Data

(63) Continuation of application No. 16/535,624, filed on Aug. 8, 2019, now Pat. No. 11,197,998, which is a
(Continued)

(51) Int. Cl.
*A61N 1/36* (2006.01)
*G16H 20/30* (2018.01)
(Continued)

(52) U.S. Cl.
CPC ..... *A61N 1/36021* (2013.01); *A61N 1/36034* (2017.08); *G06Q 10/10* (2013.01);
(Continued)

(58) Field of Classification Search
CPC ............ A61N 1/36021; A61N 1/36034; A61N 1/37235; A61N 1/40; A61N 2/02;
(Continued)

(56) References Cited

U.S. PATENT DOCUMENTS

| 3,590,810 A | 7/1971 | Kopecky |
| 4,196,737 A | 4/1980 | Bevilacqua |

(Continued)

FOREIGN PATENT DOCUMENTS

| EP | 1967226 | 9/2008 |
| EP | 1967226 | 10/2008 |

(Continued)

OTHER PUBLICATIONS

Greicius et al., Functional connectivity in the resting brain: A network analysis of the default mode hypothesis, PNAS, Jan. 2003, vol. 100, No. 1, pp. 253-258.
(Continued)

*Primary Examiner* — Amanda K Hulbert
*Assistant Examiner* — Natasha Patel
(74) *Attorney, Agent, or Firm* — Farber LLC

(57) ABSTRACT

Devices, systems and methods are disclosed that allow a patient to self-treat a medical condition, such as migraine headache, by electrical noninvasive stimulation of a vagus nerve. The system comprises a stimulator that applies an electrical impulse transcutaneously through an outer skin surface of the patient. The electrical impulse includes pulses having a frequency of about 1 kHz to about 20 kHz. The device housing may transmit data to or from a patient interface device, such as a mobile phone or computer, relating to the stimulation parameters. The interface device in turn may communicate with a database contained within other computers, via a network or the internet.

23 Claims, 10 Drawing Sheets

Related U.S. Application Data continuation of application No. 15/012,689, filed on Feb. 1, 2016, now Pat. No. 10,376,696, which is a continuation of application No. 13/858,114, filed on Apr. 8, 2013, now Pat. No. 9,248,286, which is a continuation-in-part of application No. 13/603,799, filed on Sep. 5, 2012, now Pat. No. 8,918,178, which is a continuation-in-part of application No. 13/279,437, filed on Oct. 24, 2011, now Pat. No. 9,174,045, and a continuation-in-part of application No. 13/222,087, filed on Aug. 31, 2011, now Pat. No. 9,174,066, and a continuation-in-part of application No. 13/183,721, filed on Jul. 15, 2011, now Pat. No. 8,676,324, and a continuation-in-part of application No. 13/183,765, filed on Jul. 15, 2011, now Pat. No. 8,874,227, and a continuation-in-part of application No. 13/109,250, filed on May 17, 2011, now Pat. No. 8,676,330, which is a continuation-in-part of application No. 13/075,746, filed on Mar. 30, 2011, now Pat. No. 8,874,205, which is a continuation-in-part of application No. 13/005,005, filed on Jan. 12, 2011, now Pat. No. 8,868,177, which is a continuation-in-part of application No. 12/964,050, filed on Dec. 9, 2010, now abandoned, which is a continuation-in-part of application No. 12/859,568, filed on Aug. 19, 2010, now Pat. No. 9,037,247, which is a continuation-in-part of application No. 12/612,177, filed on Nov. 4, 2009, now Pat. No. 8,041,428, and a continuation-in-part of application No. 12/408,131, filed on Mar. 20, 2009, now Pat. No. 8,812,112.

(60) Provisional application No. 61/752,895, filed on Jan. 15, 2013, provisional application No. 61/488,208, filed on May 20, 2011, provisional application No. 61/487,439, filed on May 18, 2011, provisional application No. 61/471,405, filed on Apr. 4, 2011, provisional application No. 61/451,259, filed on Mar. 10, 2011, provisional application No. 61/415,469, filed on Nov. 19, 2010.

(51) Int. Cl.
| | |
|---|---|
| *G06Q 10/10* | (2012.01) |
| *G16H 20/40* | (2018.01) |
| *G16H 40/20* | (2018.01) |
| *A61N 1/372* | (2006.01) |
| *A61N 1/04* | (2006.01) |
| *A61N 1/40* | (2006.01) |
| *A61N 2/00* | (2006.01) |
| *A61N 2/02* | (2006.01) |
| *A61B 5/00* | (2006.01) |

(52) U.S. Cl.
CPC ............ *G16H 20/30* (2018.01); *G16H 20/40* (2018.01); *G16H 40/20* (2018.01); *A61B 5/4836* (2013.01); *A61B 2560/0456* (2013.01); *A61N 1/0456* (2013.01); *A61N 1/37235* (2013.01); *A61N 1/40* (2013.01); *A61N 2/006* (2013.01); *A61N 2/008* (2013.01); *A61N 2/02* (2013.01)

(58) Field of Classification Search
CPC ...... A61N 2/006; A61N 1/0456; A61N 2/008; G16H 40/20; G16H 20/30; G16H 20/40; G06Q 10/10; A61B 2560/0456; A61B 5/4836

See application file for complete search history.

(56) References Cited

U.S. PATENT DOCUMENTS

| | | | |
|---|---|---|---|
| 4,989,605 | A | 2/1991 | Rossen |
| 5,109,847 | A | 5/1992 | Liss et al. |
| 5,458,141 | A | 10/1995 | Neil |
| 5,487,759 | A | 1/1996 | Bastyr et al. |
| 5,514,175 | A * | 5/1996 | Kim ................... A61H 39/002 607/136 |
| 5,782,874 | A | 7/1998 | Loos |
| 5,899,922 | A | 5/1999 | Loos |
| 5,983,131 | A | 11/1999 | Weaver et al. |
| 6,341,236 | B1 | 1/2002 | Osorio et al. |
| 6,463,327 | B1 | 10/2002 | Lurie et al. |
| 6,587,719 | B1 | 7/2003 | Barrett et al. |
| 6,610,713 | B2 | 8/2003 | Tracey |
| 6,631,297 | B1 | 10/2003 | Mo |
| 7,254,444 | B2 | 8/2007 | Moore |
| 7,734,340 | B2 | 6/2010 | De Ridder |
| 7,797,041 | B2 | 9/2010 | Libbus et al. |
| 2002/0099417 | A1 | 7/2002 | Naritoku et al. |
| 2002/0183237 | A1 | 12/2002 | Puskas |
| 2002/0183804 | A1 | 12/2002 | Malaney et al. |
| 2003/0212311 | A1 | 11/2003 | Nova et al. |
| 2004/0073271 | A1 | 4/2004 | Harry et al. |
| 2004/0243182 | A1 | 12/2004 | Cohen et al. |
| 2004/0249416 | A1 | 12/2004 | Yun et al. |
| 2005/0004621 | A1* | 1/2005 | Boveja ................ A61N 1/3627 607/45 |
| 2005/0021092 | A1 | 1/2005 | Yun et al. |
| 2005/0065574 | A1 | 3/2005 | Rezai |
| 2005/0113630 | A1 | 5/2005 | Fox et al. |
| 2005/0137644 | A1 | 6/2005 | Boveja et al. |
| 2005/0143786 | A1 | 6/2005 | Boveja et al. |
| 2005/0165458 | A1 | 7/2005 | Boveja |
| 2005/0187590 | A1 | 8/2005 | Boveja et al. |
| 2005/0216062 | A1 | 9/2005 | Herbst |
| 2005/0267544 | A1 | 12/2005 | Lee et al. |
| 2006/0074284 | A1 | 4/2006 | Juola et al. |
| 2006/0074450 | A1 | 4/2006 | Boveja et al. |
| 2006/0100668 | A1 | 5/2006 | Ben-David et al. |
| 2006/0100671 | A1 | 5/2006 | Ridder |
| 2006/0173510 | A1 | 8/2006 | Besio et al. |
| 2006/0178703 | A1 | 8/2006 | Huston et al. |
| 2007/0027496 | A1 | 2/2007 | Parnis et al. |
| 2007/0038264 | A1 | 2/2007 | Jaax et al. |
| 2007/0106337 | A1 | 5/2007 | Errico et al. |
| 2007/0123952 | A1 | 5/2007 | Strother et al. |
| 2007/0142874 | A1* | 6/2007 | John ................... A61N 2/006 607/45 |
| 2007/0142886 | A1 | 6/2007 | Fischell et al. |
| 2007/0150006 | A1 | 6/2007 | Libbus et al. |
| 2007/0156182 | A1 | 7/2007 | Castel et al. |
| 2007/0276449 | A1 | 11/2007 | Gunter et al. |
| 2008/0021512 | A1 | 1/2008 | Knudson et al. |
| 2008/0027513 | A1 | 1/2008 | Carbunaru |
| 2008/0045776 | A1 | 2/2008 | Fischell et al. |
| 2008/0051852 | A1 | 2/2008 | Dietrich |
| 2008/0077192 | A1 | 3/2008 | Harry et al. |
| 2008/0114199 | A1 | 5/2008 | Riehl et al. |
| 2008/0132962 | A1* | 6/2008 | DiUbaldi ............ A61N 1/36007 607/2 |
| 2008/0132964 | A1 | 6/2008 | Cohen et al. |
| 2008/0177190 | A1 | 7/2008 | Libbus et al. |
| 2008/0208266 | A1 | 8/2008 | Lesser et al. |
| 2008/0306325 | A1 | 12/2008 | Burnett et al. |
| 2009/0036945 | A1 | 2/2009 | Chancellor |
| 2009/0099622 | A1 | 4/2009 | Fowler |
| 2009/0112283 | A1 | 4/2009 | Kriksunov et al. |
| 2009/0132018 | A1 | 5/2009 | DiUbaldi et al. |
| 2009/0157149 | A1 | 6/2009 | Wahlgren et al. |
| 2009/0234417 | A1 | 9/2009 | Pastena et al. |
| 2009/0234419 | A1 | 9/2009 | Maschino et al. |
| 2009/0240297 | A1 | 9/2009 | Shavit et al. |
| 2009/0287035 | A1 | 11/2009 | Dietrich et al. |
| 2010/0030299 | A1 | 2/2010 | Covalin |
| 2010/0152794 | A1 | 6/2010 | Radivojevic et al. |
| 2010/0286553 | A1 | 11/2010 | Feler et al. |

(56) References Cited

U.S. PATENT DOCUMENTS

| | | | |
|---|---|---|---|
| 2011/0046432 | A1 | 2/2011 | Simon et al. |
| 2011/0152967 | A1 | 6/2011 | Simon et al. |
| 2011/0213295 | A1 | 9/2011 | Henley et al. |
| 2011/0224749 | A1 | 9/2011 | Ben-David et al. |
| 2011/0230701 | A1 | 9/2011 | Simon et al. |
| 2012/0029601 | A1 | 2/2012 | Simon et al. |
| 2012/0283697 | A1 | 11/2012 | Kim et al. |
| 2012/0303080 | A1 | 11/2012 | Ben-David et al. |
| 2013/0006322 | A1 | 1/2013 | Tai |
| 2013/0060304 | A1 | 3/2013 | LaTendresse et al. |
| 2013/0245486 | A1 | 9/2013 | Simon et al. |
| 2014/0005743 | A1 | 1/2014 | Giuffrida et al. |
| 2014/0172041 | A1 | 6/2014 | Draghici |
| 2014/0222102 | A1 | 8/2014 | Lemus |
| 2014/0236040 | A1 | 8/2014 | Moon |
| 2014/0031895 | A1 | 10/2014 | Rahimi |
| 2015/0165226 | A1 | 6/2015 | Simon et al. |
| 2015/0190637 | A1 | 7/2015 | Simon et al. |

FOREIGN PATENT DOCUMENTS

| | | |
|---|---|---|
| EP | 2777764 | 8/2015 |
| JP | 2006-515192 | 11/2006 |
| JP | 2009-125263 | 6/2009 |
| JP | 2012-52385 | 9/2013 |
| JP | 2014-510586 | 5/2014 |
| KR | 10-1242190 | 3/2013 |
| KR | 101242190 | 3/2013 |
| WO | WO1993/01862 | 2/1993 |
| WO | WO2005/007120 | 1/2005 |
| WO | WO2007/092062 | 8/2007 |
| WO | WO2008/042902 | 4/2008 |
| WO | WO2007/058780 | 5/2008 |
| WO | WO2009/021080 | 2/2009 |
| WO | WO2009/064641 | 5/2009 |
| WO | WO2009/135693 | 11/2009 |
| WO | WO2012/121750 | 9/2012 |
| WO | WO 2012/174330 | 12/2012 |
| WO | WO2013/066135 | 5/2013 |

OTHER PUBLICATIONS

Heneka et al., Locus ceruleus controls Alzheimer's disease pathology by modulating microglial functions through norepinephrine, PNAS, Mar. 2010, vol. 107, No. 13, pp. 6058-6063.

Lee et al., Clustering of Resting State Networks, PLoS One, Jul. 2012, vol. 7, Issue 7, pp. 1-12.

International Search Report and Written Opinion dated Aug. 25, 2015 in related Application No. PCT/US15/31847 filed May 20, 2015 (10 pages).

International Search Report and Written Opinion dated May 8, 2007 in related PCT Application No. PCT/US2006/042823 filed Nov. 2, 2006 (5 pages).

International Search Report and Written Opinion dated Sep. 17, 2007 in related PCT Application No. PCT/US2006/042828 filed Nov. 2, 2006 (5 pages).

International Search Report and Written Opinion dated Mar. 26, 2008 in related PCT Application No. PCT/US2006/042752 filed Nov. 1, 2006 (7 pages).

International Search Report and Written Opinion dated Dec. 22, 2011 in related PCT Application No. PCT/US2011/049844 filed Aug. 31, 2011 (9 pages).

KR101242190 dated Mar. 25, 2013, Espacenet computer generated English translation (11 pages).

International Search Report and Written Opinion dated Apr. 30, 2013 in related PCT Application No. PCT/US2013/023014 filed Jan. 24, 2013 (7 pages).

International Search Report and Written Opinion dated Dec. 11, 2013 in related PCT Application No. PCT/US2013/058079 filed Sep. 4, 2013 (8 pages).

International Search Report and Written Opinion dated Jan. 29, 2014 in related PCT Application No. PCT/US2013/068804 filed Nov. 6, 2013 (10 pages).

Europe Office Action dated Apr. 24, 2018 in related Application No. 15796247.3 filed May 20, 2015 (6 pages).

Europe Office Action dated Jul. 26, 2018 in related Application No. 11818591.7 filed Aug. 12, 2011 (8 pages).

* cited by examiner

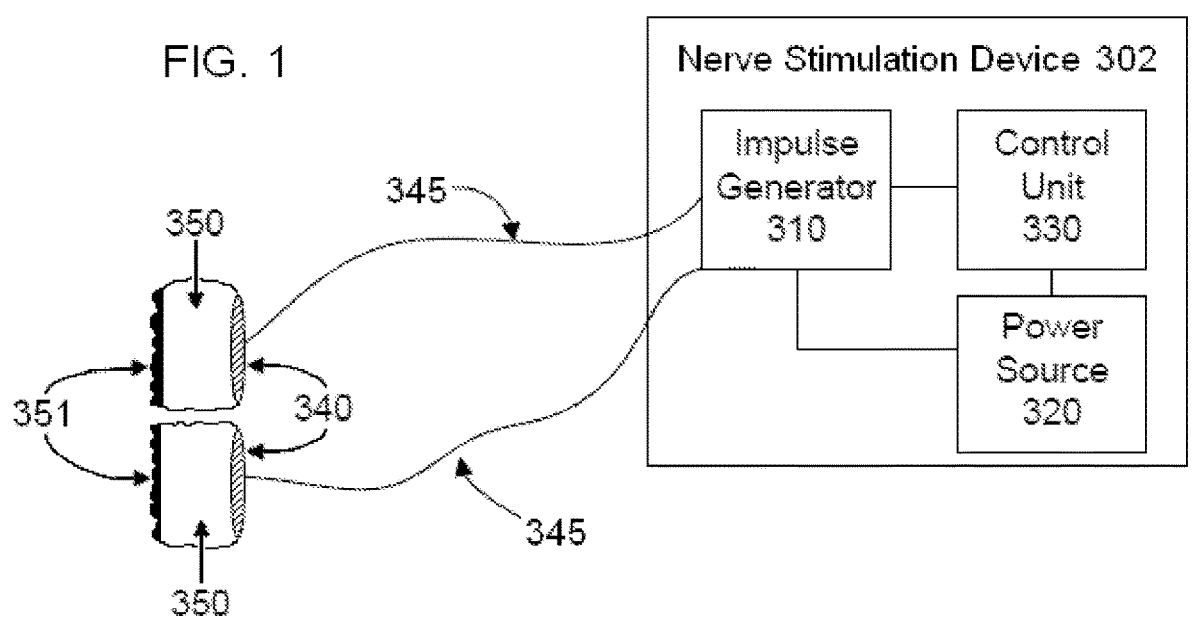

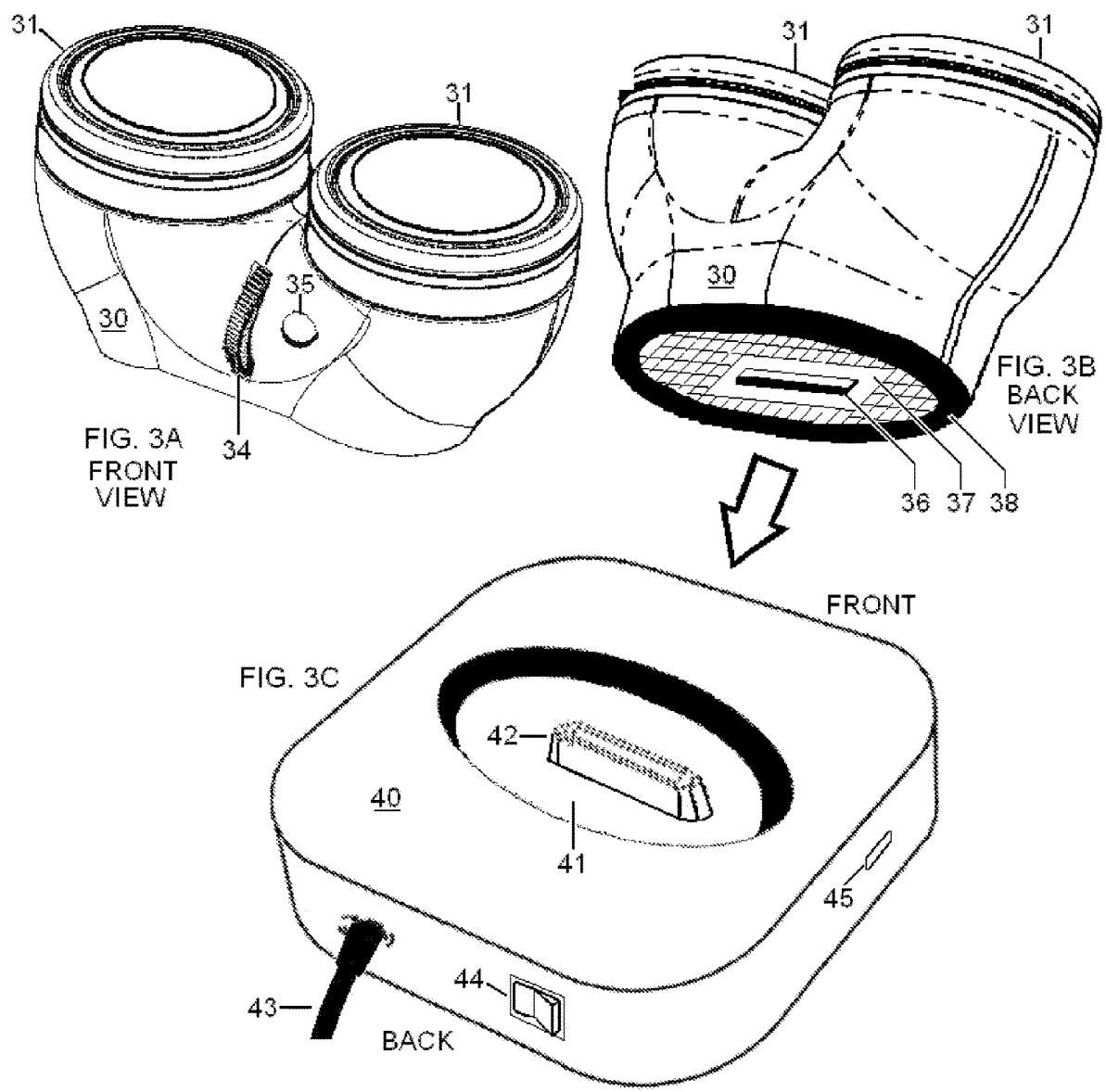

NON-INVASIVE VAGUS NERVE STIMULATION

CROSS REFERENCE TO RELATED APPLICATIONS

The present application is a continuation of U.S. Nonprovisional application Ser. No. 16/535,624, filed Aug. 8, 2019, which is a continuation of U.S. Nonprovisional application Ser. No. 15/012,689 filed 1 Feb. 2016, which is a continuation of U.S. Nonprovisional application Ser. No. 13/858,114 filed Apr. 8, 2013 now U.S. Pat. No. 9,248,286 issued 2 Feb. 2016, which (1) claims the benefit of U.S. Provisional Application Ser. No. 61/752,895 filed Jan. 15, 2013, and (2) is a continuation-in-part of U.S. Nonprovisional application Ser. No. 13/603,799 filed Sep. 5, 2012 now U.S. Pat. No. 8,918,178 issued Dec. 23, 2014, which (a) is a continuation-in-part of U.S. Nonprovisional application Ser. No. 13/279,437 filed Oct. 24, 2011 now U.S. Pat. No. 9,174,045 issued Nov. 3, 2015, and (b) is a continuation-in-part of U.S. Nonprovisional application Ser. No. 13/222,087 filed Aug. 31, 2011 now U.S. Pat. No. 9,174,066 issued Nov. 3, 2015, which is a continuation-in-part of U.S. Nonprovisional application Ser. No. 13/183,765 filed Jul. 15, 2011 now U.S. Pat. No. 8,874,227 issued Mar. 18, 2014, which (i) claims the benefit of priority of U.S. Provisional Application Ser. No. 61/488,208 filed May 20, 2011, and (ii) is a continuation-in-part of U.S. Nonprovisional application Ser. No. 13/183,721 filed Jul. 15, 2011 now U.S. Pat. No. 8,676,324 issued Mar. 18, 2014, which (A) claims the benefit of priority of U.S. Provisional Application Ser. No. 61/487,439 filed May 18, 2011, and (B) is a continuation-in-part of U.S. Nonprovisional application Ser. No. 13/109,250 filed May 17, 2011 now U.S. Pat. No. 8,676,330, issued Mar. 18, 2014, which (I) claims the benefit of priority of U.S. Provisional Application Ser. No. 61/471,405 filed Apr. 4, 2011, and (II) is a continuation-in-part of U.S. Nonprovisional application Ser. No. 13/075,746 filed Mar. 30, 2011 now U.S. Pat. No. 8,874,205 issued Oct. 28, 2014, which 1) claims the benefit of priority of U.S. Provisional Application 61/451,259 filed Mar. 10, 2011, and 2) is a continuation-in-part of U.S. Nonprovisional application Ser. No. 13/005,005 filed Jan. 12, 2011 now U.S. Pat. No. 8,868,177 issued Oct. 21, 2014, which is a continuation-in-part of U.S. Nonprovisional application Ser. No. 12/964,050 filed Dec. 9, 2010 now abandoned, which a) claims the benefit of priority of U.S. Provisional Application Ser. No. 61/415,469 filed Nov. 19, 2010, and b) is a continuation-in-part of U.S. Nonprovisional application Ser. No. 12/859,568 filed Aug. 19, 2010 now U.S. Pat. No. 9,037,247 issued May 19, 2015, which i) is a continuation-in-part application of U.S. Nonprovisional application Ser. No. 12/612,177 filed Nov. 4, 2009 now U.S. Pat. No. 8,041,428 issued Oct. 18, 2011, and ii) is a continuation-in-part of U.S. Nonprovisional application Ser. No. 12/408,131 filed Mar. 20, 2009 now U.S. Pat. No. 8,812,112 issued Aug. 19, 2014; each of which is incorporated herein by reference in its entirety.

BACKGROUND OF THE INVENTION

The field of the present invention relates to the delivery of energy impulses (and/or fields) to bodily tissues for therapeutic purposes. The invention relates more specifically to devices and methods for treating medical conditions such as migraine headaches, wherein the patient uses the devices and methods as self-treatment, without the direct assistance of a healthcare professional. The energy impulses (and/or fields) that are used to treat those conditions comprise electrical and/or electromagnetic energy, delivered non-invasively to the patient, particularly to a vagus nerve of the patient.

The use of electrical stimulation for treatment of medical conditions is well known. One of the most successful applications of modern understanding of the electrophysiological relationship between muscle and nerves is the cardiac pacemaker. Although origins of the cardiac pacemaker extend back into the 1800's, it was not until 1950 that the first practical, albeit external and bulky, pacemaker was developed. The first truly functional, wearable pacemaker appeared in 1957, and in 1960, the first fully implantable pacemaker was developed.

Around this time, it was also found that electrical leads could be connected to the heart through veins, which eliminated the need to open the chest cavity and attach the lead to the heart wall. In 1975 the introduction of the lithium-iodide battery prolonged the battery life of a pacemaker from a few months to more than a decade. The modern pacemaker can treat a variety of different signaling pathologies in the cardiac muscle, and can serve as a defibrillator as well (see U.S. Pat. No. 6,738,667 to DENO, et al., the disclosure of which is incorporated herein by reference). Because the leads are implanted within the patient, the pacemaker is an example of an implantable medical device.

Another such example is electrical stimulation of the brain with implanted electrodes (deep brain stimulation), which has been approved for use in the treatment of various conditions, including pain and movement disorders such as essential tremor and Parkinson's disease [Joel S. PERLMUTTER and Jonathan W. Mink. Deep brain stimulation. Annu. Rev. Neurosci 29 (2006):229-257].

Another application of electrical stimulation of nerves is the treatment of radiating pain in the lower extremities by stimulating the sacral nerve roots at the bottom of the spinal cord [Paul F. WHITE, Shitong Li and Jen W. Chiu. Electroanalgesia: Its Role in Acute and Chronic Pain Management. Anesth Analg 92(2001):505-513; patent U.S. Pat. No. 6,871,099, entitled Fully implantable microstimulator for spinal cord stimulation as a therapy for chronic pain, to WHITEHURST, et al].

The form of electrical stimulation that is most relevant to the present invention is vagus nerve stimulation (VNS, also known as vagal nerve stimulation). It was developed initially for the treatment of partial onset epilepsy and was subsequently developed for the treatment of depression and other disorders. The left vagus nerve is ordinarily stimulated at a location within the neck by first surgically implanting an electrode there and then connecting the electrode to an electrical stimulator [U.S. Pat. No. 4,702,254 entitled Neurocybernetic prosthesis, to ZABARA; U.S. Pat. No. 6,341,236 entitled Vagal nerve stimulation techniques for treatment of epileptic seizures, to OSORIO et al; U.S. Pat. No. 5,299,569 entitled Treatment of neuropsychiatric disorders by nerve stimulation, to WERNICKE et al; G. C. ALBERT, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009):1042-1060; GROVES D A, Brown V J. Vagal nerve stimulation: a review of its applications and potential mechanisms that mediate its clinical effects. Neurosci Biobehav Rev 29(2005):493-500; Reese TERRY, Jr. Vagus nerve stimulation: a proven therapy for treatment of epilepsy strives to improve efficacy and expand applications. Conf Proc IEEE Eng Med Biol Soc. 2009; 2009:4631-4634;

Timothy B. MAPSTONE. Vagus nerve stimulation: current concepts. Neurosurg Focus 25 (3,2008):E9, pp. 1-4; ANDREWS, R. J. Neuromodulation. I. Techniques-deep brain stimulation, vagus nerve stimulation, and transcranial magnetic stimulation. Ann. N. Y. Acad. Sci. 993(2003):1-13; LABINER, D. M., Ahern, G. L. Vagus nerve stimulation therapy in depression and epilepsy: therapeutic parameter settings. Acta. Neurol. Scand. 115(2007):23-33].

Many such therapeutic applications of electrical stimulation involve the surgical implantation of electrodes within a patient. In contrast, devices used for the procedures that are disclosed here do not involve surgery, i.e., they are not implantable medical devices. Instead, the present devices and methods stimulate nerves by transmitting energy to nerves and tissue non-invasively. A medical procedure is defined as being non-invasive when no break in the skin (or other surface of the body, such as a wound bed) is created through use of the method, and when there is no contact with an internal body cavity beyond a body orifice (e.g, beyond the mouth or beyond the external auditory meatus of the ear). Such non-invasive procedures are distinguished from invasive procedures (including minimally invasive procedures) in that the invasive procedures insert a substance or device into or through the skin (or other surface of the body, such as a wound bed) or into an internal body cavity beyond a body orifice.

For example, transcutaneous electrical stimulation of a nerve is non-invasive because it involves attaching electrodes to the skin, or otherwise stimulating at or beyond the surface of the skin or using a form-fitting conductive garment, without breaking the skin [Thierry KELLER and Andreas Kuhn. Electrodes for transcutaneous (surface) electrical stimulation. Journal of Automatic Control, University of Belgrade 18(2,2008):35-45; Mark R. PRAUSNITZ. The effects of electric current applied to skin: A review for transdermal drug delivery. Advanced Drug Delivery Reviews 18 (1996) 395-425]. In contrast, percutaneous electrical stimulation of a nerve is minimally invasive because it involves the introduction of an electrode under the skin, via needle-puncture of the skin.

Another form of non-invasive electrical stimulation is magnetic stimulation. It involves the induction, by a time-varying magnetic field, of electrical fields and current within tissue, in accordance with Faraday's law of induction. Magnetic stimulation is non-invasive because the magnetic field is produced by passing a time-varying current through a coil positioned outside the body. An electric field is induced at a distance, causing electric current to flow within electrically conducting bodily tissue. The electrical circuits for magnetic stimulators are generally complex and expensive and use a high current impulse generator that may produce discharge currents of 5,000 amps or more, which is passed through the stimulator coil to produce a magnetic pulse. The principles of electrical nerve stimulation using a magnetic stimulator, along with descriptions of medical applications of magnetic stimulation, are reviewed in: Chris HOVEY and Reza Jalinous, The Guide to Magnetic Stimulation, The Magstim Company Ltd, Spring Gardens, Whitland, Carmarthenshire, SA34 0HR, United Kingdom, 2006. In contrast, the magnetic stimulators that have been disclosed by the present Applicant are relatively simpler devices that use considerably smaller currents within the stimulator coils. Accordingly, they are intended to satisfy the need for simple-to-use and less expensive non-invasive magnetic stimulation devices.

Potential advantages of such non-invasive medical methods and devices relative to comparable invasive procedures are as follows. The patient may be more psychologically prepared to experience a procedure that is non-invasive and may therefore be more cooperative, resulting in a better outcome. Non-invasive procedures may avoid damage of biological tissues, such as that due to bleeding, infection, skin or internal organ injury, blood vessel injury, and vein or lung blood clotting. Non-invasive procedures are generally painless and may be performed without the dangers and costs of surgery. They are ordinarily performed even without the need for local anesthesia. Less training may be required for use of non-invasive procedures by medical professionals. In view of the reduced risk ordinarily associated with non-invasive procedures, some such procedures may be suitable for use by the patient or family members at home or by first-responders at home or at a workplace. Furthermore, the cost of non-invasive procedures may be significantly reduced relative to comparable invasive procedures.

In co-pending, commonly assigned patent applications, Applicant disclosed noninvasive electrical and magnetic vagus nerve stimulation devices, which are adapted, and for certain applications improved, in the present disclosure [application 13/183,765 and Publication US2011/0276112, entitled Devices and methods for non-invasive capacitive electrical stimulation and their use for vagus nerve stimulation on the neck of a patient, to SIMON et al.; application Ser. No. 12/964,050 and Publication US2011/0125203, entitled Magnetic Stimulation Devices and Methods of Therapy, to SIMON et al.; and other co-pending commonly assigned applications that are cited therein, which are herein incorporated by reference]. The present disclosure elaborates on the electrical stimulation device, rather than the magnetic stimulation device that has similar functionality, with the understanding that unless it is otherwise indicated, the elaboration could apply to either the electrical or the magnetic nerve stimulation device. Because the earlier devices have already been disclosed, the present disclosure focuses on what is new with respect to the earlier disclosures.

In the present disclosure, the stimulator is ordinarily applied by the patient himself or herself, without the benefit of having a trained healthcare provider nearby. The primary advantage of the self-stimulation therapy is that it can be administered more or less immediately when symptoms occur, rather than having to visit the healthcare provider at a clinic or emergency room. The need for such a visit would only compound the aggravation that the patient is already experiencing. Another advantage of the self-stimulation therapy is the convenience of providing the therapy in the patient's home or workplace, which eliminates scheduling difficulties, for example, when the nerve stimulation is being administered for prophylactic reasons at odd hours of the day. Furthermore, the cost of the treatment may be reduced by not requiring the involvement of a trained healthcare provider.

An exemplary teaching of the present invention is the treatment of migraine and other primary headaches such as cluster headaches, including sinus symptoms ("sinus" headaches) irrespective of whether those symptoms arise from an allergy that is co-morbid with the headache. However, it is understood that electrical stimulation by the disclosed methods and devices may be used to treat other conditions as well, including conditions described in the cited co-pending, commonly assigned patent applications.

Chronic daily headache by definition occurs with a frequency of at least 15 headache days per month for greater than 3 months duration. Chronic migraine sufferers comprise a subset of the population of chronic headache sufferers, as do those who suffer other primary headache disorders such as chronic tension-type headache [Bert B. VARGAS, David W. Dodick. The Face of Chronic Migraine: Epidemiology, Demographics, and Treatment Strategies. Neurol Clin 27 (2009) 467-479; Peter J. GOADSBY, Richard B. Lipton, Michel D. Ferrari. Migraine—Current understanding and treatment. N Engl J Med 346 (4,2002): 257-270; Stephen D SILBERSTEIN. Migraine. LANCET 363 (2004):381-391].

A migraine headache typically passes through the following stages: prodrome, aura, headache pain, and postdrome. All these phases do not necessarily occur, and there is not necessarily a distinct onset or end of each stage, with the possible exception of the aura. An interictal period follows the postdrome, unless the postrome of one migraine attack overlaps the prodrome of the next migraine attack.

The prodrome stage comprises triggering events followed by premonitory symptoms. The prodrome is often characterized by fatigue, sleepiness, elation, food cravings, depression, irritability, among other symptoms. Triggers (also called precipitating factors) such as excessive stress or sensory barrage usually precede the attack by less than 48 h. The average duration of the prodrome is 6 to 10 hours, but in half of migraine attacks, the prodrome is less than two hours (or absent), and in approximately 15% of migraine attacks, the prodrome lasts for 12 hours to 2 days.

The aura is due to cortical spreading depression within the brain. Approximately 20-30% of migraine sufferers experience an aura, ordinarily a visual aura, which is perceived as a scintillating scotoma (zig-zag line) that moves within the visual field. However, aura symptoms, regardless of their form, vary to a great extent in duration and severity from patient to patient, and also within the same individual.

Although the headache phase can begin at any hour, it most commonly begins as mild pain when the patient awakens in the morning. It then gradually builds at variable rates to reach a peak at which the pain is usually described as moderate to severe. Migraine headaches often occur on both sides of the head in children, but an adult pattern of unilateral pain often emerges in adolescence. The pain is often reported as starting in the occipital/neck regions, later becoming frontotemporal. It is throbbing and aggravated by physical effort, with all stimuli tending to accentuate the headache. The pain phase lasts 4-72 h in adults and 1-72 h in children, with a mean duration generally of less than 1 day. The pain intensity usually follows a smooth curve with a crescendo with a diminuendo. After the headache has resolved, many patients are left with a postdrome that lingers for one to two days. The main complaints during the prodrome are cognitive difficulties, such as mental tiredness.

For the present medical applications, an electrical stimulator device is ordinarily applied to the patient's neck. In a preferred embodiment of the invention, the stimulator comprises two electrodes that lie side-by-side within separate stimulator heads, wherein the electrodes are separated by electrically insulating material. Each electrode and the patient's skin are in connected electrically through an electrically conducting medium that extends from the skin to the electrode. The level of stimulation power may be adjusted with a wheel that also serves as an on/off switch.

The position and angular orientation of the device are adjusted about a location on the neck until the patient perceives stimulation when current is passed through the stimulator electrodes. The applied current is increased gradually, first to a level wherein the patient feels sensation from the stimulation. The power is then increased, but is set to a level that is less than one at which the patient first indicates any discomfort. The stimulator signal waveform may have a frequency and other parameters that are selected to produce a therapeutic result in the patient.

The electrical stimulation is then typically applied for 5 to 30 minutes, which is often sufficient to at least partially relieve headache pain within 5 minutes. The treatment then causes patients to experience a very rapid relief from headache pain, as well as a rapid opening of the nasal passages within approximately 20 minutes. Effects of the treatment may last for 4 to 5 hours or longer.

For more background information on the use of noninvasive vagus nerve stimulation to treat migraine/sinus headaches, refer to co-pending, commonly assigned application number U.S. Ser. No. 13/109,250 with publication number US20110230701, entitled Electrical and magnetic stimulators used to treat migraine/sinus headache and comorbid disorders to SIMON et al; and application number U.S. Ser. No. 13/183,721 with publication number US20110276107, entitled Electrical and magnetic stimulators used to treat migraine/sinus headache, rhinitis, sinusitis, rhinosinusitis, and comorbid disorders, to SIMON et al, which are incorporated by reference.

Despite the advantages of having a patient administer the nerve stimulation by himself or herself, such self-stimulation presents certain risks and difficulties relating to safety and efficacy. In some situations, the vagus nerve stimulator should be applied to the left or to the right vagus nerve, but not vice versa. For example, if the stimulator is applied to the left vagus nerve at the neck, it would work as prescribed, but if it were to be accidentally applied to the right vagus nerve, the device could potentially cause cardiac problems. On the other hand, in some situations the stimulation may actually be most beneficial if applied to the right vagus nerve, and it may be relatively less effective if applied to the left vagus nerve. Therefore, if the patient is using the vagus nerve stimulator by himself or herself, it would be useful for the device be designed so that it can be used only on the prescribed side of the neck. The present invention discloses several methods for preventing inadvertent stimulation on the side of the neck that is not prescribed.

Another issue concerns the positioning of the vagus nerve stimulator on the neck of the patient. Although the stimulator is designed to be robust against very small variations in position of the stimulator relative to the vagus nerve, there is nevertheless an optimal position that would preferably be maintained throughout the stimulation session in order to achieve maximum effectiveness from the stimulation. The patient will sense whether the nerve is being stimulated and can adjust the position of the stimulator in search for the optimum, but the patient also has the option of adjusting the amplitude of the stimulation in an attempt to compensate for a sub-optimal position. However, the ability to compensate using stimulation-amplitude control is limited by the likelihood that the skin and other tissue in the vicinity of the nerve may become uncomfortable if the amplitude of stimulation becomes too high. A related problem is that fluctuating movement of the stimulator relative to nerve being stimulated is to some extent unavoidable, due for example to neck muscle contractions that accompany breathing. The combination of sub-optimal positioning of the device on the neck and unavoidable movement of the device makes it difficult to assure that the patient is receiving exactly the prescribed stimulation dose in each stimulation session.

Another problem is that the patient may wish to stop the stimulation session based only on some subjective assessment of whether the stimulation has sufficiently relieved the symptoms. However, there may be a diminishing effectiveness if the stimulation session is too long, for the following reason. Let the numerical value of the accumulated effects of vagus nerve stimulation be denoted as S(t). It may for present exemplary purposes be represented as a function that increases at a rate proportional to the stimulation voltage V in the vicinity of the nerve and decays with a time constant $\tau_P$, such that after prolonged stimulation, the accumulated stimulation effectiveness may saturate at a value equal to the product of V and $\tau_P$. Thus, if $T_P$ is the duration of a vagus nerve stimulation in a particular treatment session, then for time t<$T_P$, S(t)=V$\tau_P$ [1−exp(−t/$\tau_P$)]+$S_0$ exp(−t/$\tau_P$), and for t>$T_P$, S(t)=S($T_P$) exp (−[t−$T_P$]/$\tau_P$), where the time t is measured from the start of a stimulus, and $S_0$ is the value of S when t=0. The optimal duration of a stimulation session may be different from patient to patient, because the decay time constant $\tau_P$ may vary from patient to patient. To the extent that the stimulation protocol is designed to treat each patient individually, such that subsequent treatment sessions are designed in view of the effectiveness of previous treatment sessions, it is would be useful for the stimulation amplitude V be as constant as possible, and the treatment session should take into account the above-mentioned principle of diminishing returns. At a minimum, the average stimulation amplitude in a session should be estimated or evaluated, despite movement of the stimulator relative to the nerve and despite amplitude adjustment by the patient.

These potential problems, related to placement and movement of the stimulator, do not arise in patients in whom a stimulator electrode has been implanted about a vagus nerve. They are also of minor significance in situations where a healthcare provider is responsible for careful usage of noninvasive stimulator devices, rather than the patient. More generally, when the patient performs self-stimulation with the nerve stimulator, practical matters arise such as: how to maintain and charge the stimulator device, how to enable the patient to initiate a stimulation session, how to design the stimulation session based on the present medical circumstances of the patient, how to monitor operation of the device taking into account all of the factors that may influence a successful treatment session, and how to evaluate the success of the treatment session when it is finished. Furthermore, when the patient is able to perform self-stimulation, administrative matters such as maintaining medical records and billing must be addressed. The present invention is intended to address many such problems. The invention comprises several components, each of which may be involved in the solution of different problems, such that the system as a whole is more functional than the component parts considered individually.

SUMMARY OF THE INVENTION

The present invention involves devices and methods for the self-treatment of a medical condition by a patient, who stimulates a selected nerve electrically. Devices are disclosed that allow the stimulation to be performed noninvasively, wherein electrodes are placed against the skin of the patient. In preferred embodiments of the invention, the selected nerve is a vagus nerve that lies under the skin of the patient's neck. The disclosure uses the treatment of migraine headaches as the exemplary medical condition.

The system comprises a dual-electrode stimulator housing that is applied to the surface of the patient's neck, as well as a docking station that is used to charge a rechargeable battery within the stimulator housing. The docking station and stimulator housing also transmit data to one another regarding the status of a stimulation session, prior to and after the session and possibly also during the session. They also transmit data to and from a computer program in a patient interface device, such as a mobile phone or nearby computer. Such data transmission to and from the patient interface device is preferably wireless, but wired communication between devices is also contemplated. The interface device, and possibly the stimulator or docking station, in turn communicates with other computers containing medical record and billing databases, via the internet. Methods are described wherein medical records are used and updated during the course of a stimulation session, and wherein payment for a treatment session is made.

The system is designed to address particular problems that arise during self-treatment, when a medical professional is not present. Such problems include assuring that the patient stimulates a vagus nerve on a prescribed side of the neck (left or right), minimizing or documenting motion of the stimulator, documenting the patient's adjustment of the stimulation amplitude, and controlling the amount of energy that can be delivered to the patient during a stimulation session.

The parameters for the protocol of each stimulation session are transmitted via the docking station to the stimulator device from a physician-controlled computer, which provides authorization for the charging of the stimulator device's batteries by the docking station. Parameters of the stimulation protocol may be varied in response to heterogeneity in the symptoms of patients. Different stimulation parameters may also be selected as the course of the patient's medical condition changes. In preferred embodiments, the disclosed stimulation methods and devices do not produce clinically significant side effects, such as agitation or anxiety, or changes in heart rate or blood pressure.

In a preferred embodiment of the invention, the stimulator housing comprises a rechargeable source of electrical power and two or more remote electrodes that are configured to stimulate a deep nerve. The stimulator may comprise two electrodes that lie side-by-side within a hand-held housing, wherein the electrodes are separated by electrically insulating material. Each electrode is in continuous contact with an electrically conducting medium that extends from the patient-interface element of the stimulator to the electrode. The interface element contacts the patient's skin when the device is in operation.

Current passing through an electrode may be about 0 to 40 mA, with voltage across the electrodes of about 0 to 30 volts. The current is passed through the electrodes in bursts of pulses. There may be 1 to 20 pulses per burst, preferably five pulses. Each pulse within a burst has a duration of about 20 to 1000 microseconds, preferably 200 microseconds. A burst followed by a silent inter-burst interval repeats at 1 to 5000 bursts per second (bps, similar to Hz), preferably at 15-50 bps, and even more preferably at 25 bps. The preferred shape of each pulse is a full sinusoidal wave.

A source of power supplies a pulse of electric charge to the electrodes, such that the electrodes produce an electric current and/or an electric field within the patient. The electrical stimulator is configured to induce a peak pulse voltage sufficient to produce an electric field in the vicinity of a nerve such as a vagus nerve, to cause the nerve to depolarize and reach a threshold for action potential propagation. By way of example, the threshold electric field for stimulation of the nerve may be about 8 V/m at 1000 Hz. For example, the device may produce an electric field within the patient of about 10 to 600 V/m (preferably less than 100 V/m) and an electrical field gradient of greater than 2 V/m/mm. Electric fields that are produced at the vagus nerve are generally sufficient to excite all myelinated A and B fibers, but not necessarily the unmyelinated C fibers. However, by using a reduced amplitude of stimulation, excitation of A-delta and B fibers may also be avoided.

The preferred stimulator shapes an elongated electric field of effect that can be oriented parallel to a long nerve, such as a vagus. By selecting a suitable waveform to stimulate the nerve, along with suitable parameters such as current, voltage, pulse width, pulses per burst, inter-burst interval, etc., the stimulator produces a correspondingly selective physiological response in an individual patient. Such a suitable waveform and parameters are simultaneously selected to avoid substantially stimulating nerves and tissue other than the target nerve, particularly avoiding the stimulation of nerves in the skin that produce pain.

Treating a medical condition such as migraine headache may be implemented within the context of control theory. A controller comprising, for example, the disclosed nerve stimulator, a PID, and a feedback or feedforward model, provides input to the patient via stimulation of one or both of the patient's vagus nerves. The signals used to control the stimulation comprise physiological or environmental variables that are measured with sensors. In one embodiment, the vagus nerve stimulation is varied as a function of motion of the stimulator, which is measured using accelerometers.

The novel systems, devices and methods for treating medical condition such as migraine headache are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIG. 1 shows a schematic view of nerve modulating devices according to the present invention, which supply controlled pulses of electrical current to surface electrodes;

FIG. 3A is a perspective view of a front of a dual-electrode stimulator according to an embodiment of the present invention;

FIG. 3B is a perspective view of the back of the dual-electrode stimulator shown in FIG. 3A;

FIG. 3C illustrates an exemplary docking station for the dual-electrode stimulator of FIG. 3A;

DETAILED DESCRIPTION OF THE PREFERRED EMBODIMENTS

Figure 2A:
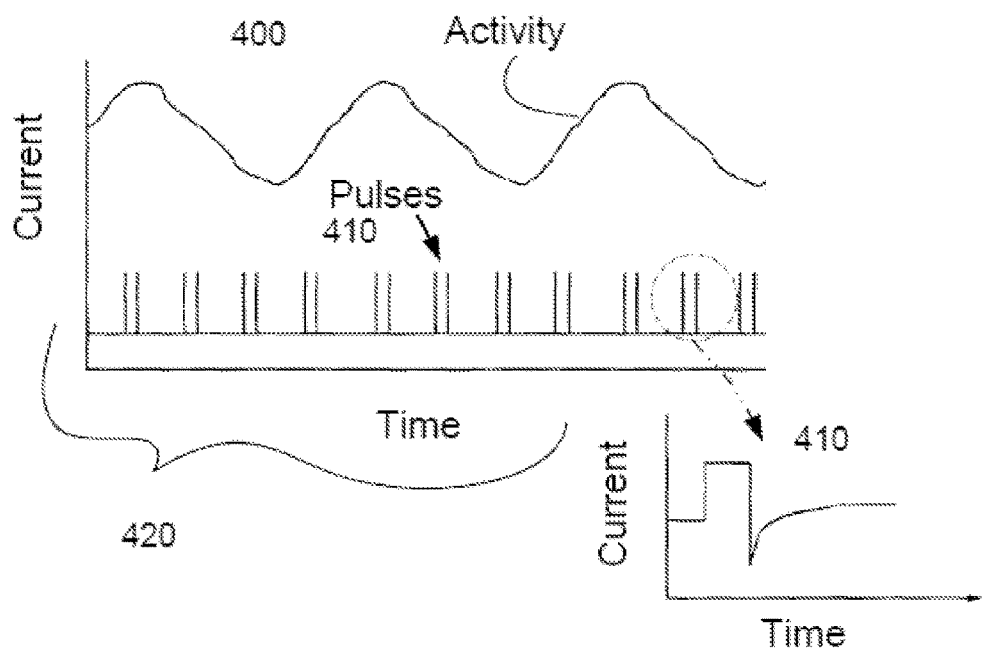
FIG. 2A shows an exemplary electrical voltage/current profile for stimulating and/or modulating impulses that are applied to a nerve according to the present invention.

In the present invention, electrodes applied to the skin of the patient generate currents within the tissue of the patient. An objective of the invention is to produce and apply the electrical impulses so as to interact with the signals of one or more nerves, in order to achieve the therapeutic result. Much of the disclosure will be directed specifically to treatment of a patient by stimulation in or around a vagus nerve, with devices positioned non-invasively on or near a patient's neck. However, it will also be appreciated that the devices and methods of the present invention can be applied to other tissues and nerves of the body, including but not limited to other parasympathetic nerves, sympathetic nerves, spinal or cranial nerves.

Description of the Nerve Stimulating/Modulating Devices

Devices of the invention that are used to stimulate a vagus nerve will now be described. An embodiment of the present invention is shown in FIG. 1, which is a schematic diagram of an electrode-based nerve stimulating/modulating device 302 for delivering impulses of energy to nerves for the treatment of medical conditions. As shown, device 302 may include an impulse generator 310; a power source 320 coupled to the impulse generator 310; a control unit 330 in communication with the impulse generator 310 and coupled to the power source 320; and electrodes 340 coupled via wires 345 to impulse generator 310. In a preferred embodiment, the same impulse generator 310, power source 320, and control unit 330 may be used for either a magnetic stimulator or the electrode-based stimulator 302, allowing the user to change parameter settings depending on whether magnetic coils or the electrodes 340 are attached.

Although a pair of electrodes 340 is shown in FIG. 1, in practice the electrodes may also comprise three or more distinct electrode elements, each of which is connected in series or in parallel to the impulse generator 310. Thus, the electrodes 340 that are shown in FIG. 1 represent all electrodes of the device collectively.

The item labeled in FIG. 1 as 350 is a volume, contiguous with an electrode 340, that is filled with electrically conducting medium. The conducting medium in which the electrode 340 is embedded need not completely surround an electrode. The volume 350 is electrically connected to the patient at a target skin surface in order to shape the current density passed through an electrode 340 that is needed to accomplish stimulation of the patient's nerve or tissue. The electrical connection to the patient's skin surface is through an interface 351. In one embodiment, the interface is made of an electrically insulating (dielectric) material, such as a thin sheet of Mylar. In that case, electrical coupling of the stimulator to the patient is capacitive. In other embodiments, the interface comprises electrically conducting material, such as the electrically conducting medium 350 itself, or an electrically conducting or permeable membrane. In that case, electrical coupling of the stimulator to the patient is ohmic. As shown, the interface may be deformable such that it is form-fitting when applied to the surface of the body. Thus, the sinuousness or curvature shown at the outer surface of the interface 351 corresponds also to sinuousness or curvature on the surface of the body, against which the interface 351 is applied, so as to make the interface and body surface contiguous.

The control unit 330 controls the impulse generator 310 to generate a signal for each of the device's coils or electrodes. The signals are selected to be suitable for amelioration of a particular medical condition, when the signals are applied non-invasively to a target nerve or tissue via the electrodes 340. It is noted that nerve stimulating/modulating device 302 may be referred to by its function as a pulse generator. Patent application publications US2005/0075701 and US2005/0075702, both to SHAFER, contain descriptions of pulse generators that may be applicable to the present invention. By way of example, a pulse generator is also commercially available, such as Agilent 33522A Function/Arbitrary Waveform Generator, Agilent Technologies, Inc., 5301 Stevens Creek Blvd Santa Clara Calif. 95051.

The control unit 330 may also comprise a general purpose computer, comprising one or more CPU, computer memories for the storage of executable computer programs (including the system's operating system) and the storage and retrieval of data, disk storage devices, communication devices (such as serial and USB ports) for accepting external signals from the system's keyboard, computer mouse, and touchscreen, as well as any externally supplied physiological signals (see FIG. 9), analog-to-digital converters for digitizing externally supplied analog signals (see FIG. 9), communication devices for the transmission and receipt of data to and from external devices such as printers and modems that comprise part of the system, hardware for generating the display of information on monitors that comprise part of the system, and busses to interconnect the above-mentioned components. Thus, the user may operate the system by typing instructions for the control unit 330 at a device such as a keyboard and view the results on a device such as the system's computer monitor, or direct the results to a printer, modem, and/or storage disk. Control of the system may be based upon feedback measured from externally supplied physiological or environmental signals. Alternatively, the control unit 330 may have a compact and simple structure, for example, wherein the user may operate the system using only an on/off switch and power control wheel or knob. In a section below, a preferred embodiment is described wherein the stimulator housing has a simple structure, but other components of the control unit 330 are distributed into other devices (see FIG. 5).

Parameters for the nerve or tissue stimulation include power level, frequency and train duration (or pulse number). The stimulation characteristics of each pulse, such as depth of penetration, strength and selectivity, depend on the rise time and peak electrical energy transferred to the electrodes, as well as the spatial distribution of the electric field that is produced by the electrodes. The rise time and peak energy are governed by the electrical characteristics of the stimulator and electrodes, as well as by the anatomy of the region of current flow within the patient. In one embodiment of the invention, pulse parameters are set in such as way as to account for the detailed anatomy surrounding the nerve that is being stimulated [Bartosz SAWICKI, Robert Szmurlo, Przemyslaw Plonecki, Jacek Starzyński, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, 105 Press, 2008]. Pulses may be monophasic, biphasic or polyphasic. Embodiments of the invention include those that are fixed frequency, where each pulse in a train has the same inter-stimulus interval, and those that have modulated frequency, where the intervals between each pulse in a train can be varied.

FIG. 2A illustrates an exemplary electrical voltage/current profile for a stimulating, blocking and/or modulating impulse applied to a portion or portions of selected nerves in accordance with an embodiment of the present invention. For the preferred embodiment, the voltage and current refer to those that are non-invasively produced within the patient by the stimulator coils or electrodes. As shown, a suitable electrical voltage/current profile 400 for the blocking and/or modulating impulse 410 to the portion or portions of a nerve may be achieved using pulse generator 310. In a preferred embodiment, the pulse generator 310 may be implemented using a power source 320 and a control unit 330 having, for instance, a processor, a clock, a memory, etc., to produce a pulse train 420 to the electrodes 340 that deliver the stimulating, blocking and/or modulating impulse 410 to the nerve. Nerve stimulating/modulating device 302 may be externally powered and/or recharged or may have its own power source 320. The parameters of the modulation signal 400, such as the frequency, amplitude, duty cycle, pulse width, pulse shape, etc., are preferably programmable. An external communication device may modify the pulse generator programming to improve treatment.

In addition, or as an alternative to the devices to implement the modulation unit for producing the electrical voltage/current profile of the stimulating, blocking and/or modulating impulse to the electrodes, the device disclosed in patent publication No. US2005/0216062 may be employed. That patent publication discloses a multifunctional electrical stimulation (ES) system adapted to yield output signals for effecting electromagnetic or other forms of electrical stimulation for a broad spectrum of different biological and biomedical applications, which produce an electric field pulse in order to non-invasively stimulate nerves. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables. Examples of the signals that may be generated by such a system are described in a publication by LIBOFF [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004)]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated, as well as the outputs of various sensors which sense prevailing conditions prevailing in this substance, whereby the user of the system can manually adjust the signal, or have it automatically adjusted by feedback, to provide an electrical stimulation signal of whatever type the user wishes, who can then observe the effect of this signal on a substance being treated.

The stimulating and/or modulating impulse signal 410 preferably has a frequency, an amplitude, a duty cycle, a pulse width, a pulse shape, etc. selected to influence the therapeutic result, namely, stimulating and/or modulating some or all of the transmission of the selected nerve. For example, the frequency may be about 1 Hz or greater, such as between about 15 Hz to 100 Hz, preferably between about 15-50 Hz and more preferably between about 15-35 Hz. In an exemplary embodiment, the frequency is 25 Hz. The modulation signal may have a pulse width selected to influence the therapeutic result, such as about 1 microseconds to about 1000 microseconds, preferably about 100-400 microseconds and more preferably about 200-400 microseconds. For example, the electric field induced or produced by the device within tissue in the vicinity of a nerve may be about 5 to 600 V/m, preferably less than 100 V/m, and even more preferably less than 30 V/m. The gradient of the electric field may be greater than 2 V/m/mm. More generally, the stimulation device produces an electric field in the vicinity of the nerve that is sufficient to cause the nerve to depolarize and reach a threshold for action potential propagation, which is approximately 8 V/m at 1000 Hz. The modulation signal may have a peak voltage amplitude selected to influence the therapeutic result, such as about 0.2 volts or greater, such as about 0.2 volts to about 40 volts, preferably between about 1-20 volts and more preferably between about 2-12 volts.

An objective of the disclosed stimulators is to provide both nerve fiber selectivity and spatial selectivity. Spatial selectivity may be achieved in part through the design of the electrode or coil configuration, and nerve fiber selectivity may be achieved in part through the design of the stimulus waveform, but designs for the two types of selectivity are intertwined. This is because, for example, a waveform may selectively stimulate only one of two nerves whether they lie close to one another or not, obviating the need to focus the stimulating signal onto only one of the nerves [GRILL W and Mortimer J T. Stimulus waveforms for selective neural stimulation. IEEE Eng. Med. Biol. 14 (1995): 375-385]. These methods complement others that are used to achieve selective nerve stimulation, such as the use of local anesthetic, application of pressure, inducement of ischemia, cooling, use of ultrasound, graded increases in stimulus intensity, exploiting the absolute refractory period of axons, and the application of stimulus blocks [John E. SWETT and Charles M. Bourassa. Electrical stimulation of peripheral nerve. In: Electrical Stimulation Research Techniques, Michael M. Patterson and Raymond P. Kesner, eds. Academic Press. (New York, 1981) pp. 243-295].

To date, the selection of stimulation waveform parameters for nerve stimulation has been highly empirical, in which the parameters are varied about some initially successful set of parameters, in an effort to find an improved set of parameters for each patient. A more efficient approach to selecting stimulation parameters might be to select a stimulation waveform that mimics electrical activity in the anatomical regions that one is attempting stimulate indirectly, in an effort to entrain the naturally occurring electrical waveform, as suggested in patent number U.S. Pat. No. 6,234,953, entitled Electrotherapy device using low frequency magnetic pulses, to THOMAS et al. and application number US20090299435, entitled Systems and methods for enhancing or affecting neural stimulation efficiency and/or efficacy, to GLINER et al. One may also vary stimulation parameters iteratively, in search of an optimal setting [U.S. Pat. No. 7,869,885, entitled Threshold optimization for tissue stimulation therapy, to BEGNAUD et al]. However, some stimulation waveforms, such as those described herein, are discovered by trial and error, and then deliberately improved upon.

Invasive nerve stimulation typically uses square wave pulse signals. However, Applicant found that square waveforms are not ideal for non-invasive stimulation as they produce excessive pain. Prepulses and similar waveform modifications have been suggested as methods to improve selectivity of nerve stimulation waveforms, but Applicant did not find them ideal [Aleksandra VUCKOVIC, Marco Tosato and Johannes J Struijk. A comparative study of three techniques for diameter selective fiber activation in the vagal nerve: anodal block, depolarizing prepulses and slowly rising pulses. J. Neural Eng. 5 (2008): 275-286; Aleksandra VUCKOVIC, Nico J. M. Rijkhoff, and Johannes J. Struijk. Different Pulse Shapes to Obtain Small Fiber Selective Activation by Anodal Blocking—A Simulation Study. IEEE Transactions on Biomedical Engineering 51(5, 2004):698-706; Kristian HENNINGS. Selective Electrical Stimulation of Peripheral Nerve Fibers: Accommodation Based Methods. Ph.D. Thesis, Center for Sensory-Motor Interaction, Aalborg University, Aalborg, Denmark, 2004].

Applicant also found that stimulation waveforms consisting of bursts of square pulses are not ideal for non-invasive stimulation [M. I. JOHNSON, C. H. Ashton, D. R. Bousfield and J. W. Thompson. Analgesic effects of different pulse patterns of transcutaneous electrical nerve stimulation on cold-induced pain in normal subjects. Journal of Psychosomatic Research 35 (2/3, 1991):313-321; U.S. Pat. No. 7,734,340, entitled Stimulation design for neuromodulation, to De Ridder]. However, bursts of sinusoidal pulses are a preferred stimulation waveform, as shown in FIGS. 2D and 2E. As seen there, individual sinusoidal pulses have a period of $\tau$, and a burst consists of N such pulses. This is followed by a period with no signal (the inter-burst period). The pattern of a burst followed by silent inter-burst period repeats itself with a period of T. For example, the sinusoidal period $\tau$ may be between about 50-1000 microseconds (equivalent to about 1-20 KHz), preferably between about 100-400 microseconds (equivalent to about 2.5-10 KHz), more preferably about 133-400 microseconds (equivalent to about 2.5-7.5 KHZ) and even more preferably about 200 microseconds (equivalent to about 5 KHz); the number of pulses per burst may be N=1-20, preferably about 2-10 and more preferably about 5; and the whole pattern of burst followed by silent inter-burst period may have a period T comparable to about 10-100 Hz, preferably about 15-50 Hz, more preferably about 25-35 Hz and even more preferably about 25 Hz (a much smaller value of T is shown in FIG. 2E to make the bursts discernable). When these exemplary values are used for T and $\tau$, the waveform contains significant Fourier components at higher frequencies (1/200 microseconds=5000/sec), as compared with those contained in transcutaneous nerve stimulation waveforms, as currently practiced.

The above waveform is essentially a 1-20 KHz signal that includes bursts of pulses with each burst having a frequency of about 10-100 Hz and each pulse having a frequency of about 1-20 KHz. Another way of thinking about the waveform is that it is a 1-20 KHz waveform that repeats itself at a frequency of about 10-100 Hz. Applicant is unaware of such a waveform having been used with vagus nerve stimulation, but a similar waveform has been used to stimulate muscle as a means of increasing muscle strength in elite athletes. However, for the muscle strengthening application, the currents used (200 mA) may be very painful and two orders of magnitude larger than what are disclosed herein. Furthermore, the signal used for muscle strengthening may be other than sinusoidal (e.g., triangular), and the parameters $\tau$, N, and T may also be dissimilar from the values exemplified above [A. DELITTO, M. Brown, M. J. Strube, S. J. Rose, and R. C. Lehman. Electrical stimulation of the quadriceps femoris in an elite weight lifter: a single subject experiment. Int J Sports Med 10(1989):187-191; Alex R WARD, Nataliya Shkuratova. Russian Electrical Stimulation: The Early Experiments. Physical Therapy 82 (10, 2002): 1019-1030; Yocheved LAUFER and Michal Elboim. Effect of Burst Frequency and Duration of Kilohertz-Frequency Alternating Currents and of Low-Frequency Pulsed Currents on Strength of Contraction, Muscle Fatigue, and Perceived Discomfort. Physical Therapy 88 (10,2008):1167-1176; Alex R WARD. Electrical Stimulation Using Kilohertz-Frequency Alternating Current. Physical Therapy 89 (2,2009):181-190; J. PETROFSKY, M. Laymon, M. Prowse, S. Gunda, and J. Batt. The transfer of current through skin and muscle during electrical stimulation with sine, square, Russian and interferential waveforms. Journal of Medical Engineering and Technology 33 (2,2009): 170-181; U.S. Pat. No. 4,177,819, entitled Muscle stimulating apparatus, to KOFSKY et al]. Burst stimulation has also been disclosed in connection with implantable pulse generators, but wherein the bursting is characteristic of the neuronal firing pattern itself [U.S. Pat. No. 7,734,340 to DE RIDDER, entitled Stimulation design for neuromodulation; application US20110184486 to DE RIDDER, entitled Combination of tonic and burst stimulations to treat neurological disorders]. By way of example, the electric field shown in FIGS. 2B and 2C may have an $E_{max}$ value of 17 V/m, which is sufficient to stimulate the nerve but is significantly lower than the threshold needed to stimulate surrounding muscle.

High frequency electrical stimulation is also known in the treatment of back pain at the spine [Patent application US20120197369, entitled Selective high frequency spinal cord modulation for inhibiting pain with reduced side effects and associated systems and methods, to ALATARIS et al.; Adrian A L KAISY, Iris Smet, and Jean-Pierre Van Buyten. Analgeia of axial low back pain with novel spinal neuromodulation. Poster presentation #202 at the 2011 meeting of The American Academy of Pain Medicine, held in National Harbor, Md., Mar. 24-27, 2011].

Those methods involve high-frequency modulation in the range of from about 1.5 KHz to about 50 KHz, which is applied to the patient's spinal cord region. However, such methods are different from the present invention because, for example, they are invasive; they do not involve a bursting waveform, as in the present invention; they necessarily involve A-delta and C nerve fibers and the pain that those fibers produce, whereas the present invention does not; they may involve a conduction block applied at the dorsal root level, whereas the present invention may stimulate action potentials without blocking of such action potentials; and/or they involve an increased ability of high frequency modulation to penetrate through the cerebral spinal fluid, which is not relevant to the present invention. In fact, a likely explanation for the reduced back pain that is produced by their use of frequencies from 10 to 50 KHz is that the applied electrical stimulus at those frequencies causes permanent damage to the pain-causing nerves, whereas the present invention involves only reversible effects [LEE RC, Zhang D, Hannig J. Biophysical injury mechanisms in electrical shock trauma. Annu Rev Biomed Eng 2(2000):477-509].

Consider now which nerve fibers may be stimulated by the non-invasive vagus nerve stimulation. The vagus nerve (tenth cranial nerve, paired left and right) is composed of motor and sensory fibers. The vagus nerve leaves the cranium, passes down the neck within the carotid sheath to the root of the neck, then passes to the chest and abdomen, where it contributes to the innervation of the viscera.

A vagus nerve in man consists of over 100,000 nerve fibers (axons), mostly organized into groups. The groups are contained within fascicles of varying sizes, which branch and converge along the nerve. Under normal physiological conditions, each fiber conducts electrical impulses only in one direction, which is defined to be the orthodromic direction, and which is opposite the antidromic direction. However, external electrical stimulation of the nerve may produce action potentials that propagate in orthodromic and antidromic directions. Besides efferent output fibers that convey signals to the various organs in the body from the central nervous system, the vagus nerve conveys sensory (afferent) information about the state of the body's organs back to the central nervous system. Some 80-90% of the nerve fibers in the vagus nerve are afferent (sensory) nerves, communicating the state of the viscera to the central nervous system.

The largest nerve fibers within a left or right vagus nerve are approximately 20 μm in diameter and are heavily myelinated, whereas only the smallest nerve fibers of less than about 1 μm in diameter are completely unmyelinated. When the distal part of a nerve is electrically stimulated, a compound action potential may be recorded by an electrode located more proximally. A compound action potential contains several peaks or waves of activity that represent the summated response of multiple fibers having similar conduction velocities. The waves in a compound action potential represent different types of nerve fibers that are classified into corresponding functional categories, with approximate diameters as follows: A-alpha fibers (afferent or efferent fibers, 12-20 μm diameter), A-beta fibers (afferent or efferent fibers, 5-12 μm), A-gamma fibers (efferent fibers, 3-7 μm), A-delta fibers (afferent fibers, 2-5 μm), B fibers (1-3 μm) and C fibers (unmyelinated, 0.4-1.2 μm). The diameters of group A and group B fibers include the thickness of the myelin sheaths. It is understood that the anatomy of the vagus nerve is developing in newborns and infants, which accounts in part for the maturation of autonomic reflexes. Accordingly, it is also understood that the parameters of vagus nerve stimulation in the present invention are chosen in such a way as to account for this age-related maturation [PEREYRA P M, Zhang W, Schmidt M, Becker L E. Development of myelinated and unmyelinated fibers of human vagus nerve during the first year of life. J Neurol Sci 110(1-2,1992):107-113; SCHECHTMAN V L, Harper R M, Kluge K A. Development of heart rate variation over the first 6 months of life in normal infants. Pediatr Res 26(4,1989):343-346].

The waveform disclosed in FIG. 2 contains significant Fourier components at high frequencies (e.g., 1/200 microseconds=5000/sec), even if the waveform also has components at lower frequencies (e.g., 25/sec). Transcutaneously, A-beta, A-delta, and C fibers are typically excited at 2000 Hz, 250 Hz, and 5 Hz, respectively, i.e., the 2000 Hz stimulus is described as being specific for measuring the response of A-beta fibers, the 250 Hz for A-delta fibers, and the 5 Hz for type C fibers [George D. BAQU IS et al. TECHNOLOGY REVIEW: THE NEUROMETER CURRENT PERCEPTION THRESHOLD (CPT). Muscle Nerve 22(Supplement 8,1999): S247-S259]. Therefore, the high frequency component of the noninvasive stimulation waveform will preferentially stimulate the A-alpha and A-beta fibers, and the C fibers will be largely unstimulated.

However, the threshold for activation of fiber types also depends on the amplitude of the stimulation, and for a given stimulation frequency, the threshold increases as the fiber size decreases. The threshold for generating an action potential in nerve fibers that are impaled with electrodes is traditionally described by Lapicque or Weiss equations, which describe how together the width and amplitude of stimulus pulses determine the threshold, along with parameters that characterize the fiber (the chronaxy and rheobase). For nerve fibers that are stimulated by electric fields that are applied externally to the fiber, as is the case here, characterizing the threshold as a function of pulse amplitude and frequency is more complicated, which ordinarily involves the numerical solution of model differential equations or a case-by-case experimental evaluation [David BOINAGROV, Jim Loudin and Daniel Palanker. Strength-Duration Relationship for Extracellular Neural Stimulation: Numerical and Analytical Models. J Neurophysiol 104(2010):2236-2248].

For example, REILLY describes a model (the spatially extended nonlinear nodal model or SENN model) that may be used to calculate minimum stimulus thresholds for nerve fibers having different diameters [J. Patrick REILLY. Electrical models for neural excitation studies. Johns Hopkins APL Technical Digest 9(1, 1988): 44-59]. According to REILLY's analysis, the minimum threshold for excitation of myelinated A fibers is 6.2 V/m for a 20 m diameter fiber, 12.3 V/m for a 10 m fiber, and 24.6 V/m for a 5 m diameter fiber, assuming a pulse width that is within the contemplated range of the present invention (1 ms). It is understood that these thresholds may differ slightly from those produced by the waveform of the present invention as illustrated by REILLY's figures, for example, because the present invention prefers to use sinusoidal rather than square pulses. Thresholds for B and C fibers are respectively 2 to 3 and 10 to 100 times greater than those for A fibers [Mark A. CASTORO, Paul B. Yoo, Juan G. Hincapie, Jason J. Hamann, Stephen B. Ruble, Patrick D. Wolf, Warren M. Grill. Excitation properties of the right cervical vagus nerve in adult dogs. Experimental Neurology 227 (2011): 62-68]. If we assume an average A fiber threshold of 15 V/m, then B fibers would have thresholds of 30 to 45 V/m and C fibers would have thresholds of 150 to 1500 V/m. The present invention produces electric fields at the vagus nerve in the range of about 6 to 100 V/m, which is therefore generally sufficient to excite all myelinated A and B fibers, but not the unmyelinated C fibers. In contrast, invasive vagus nerve stimulators that have been used for the treatment of epilepsy have been reported to excite C fibers in some patients [EVANS M S, Verma-Ahuja S, Naritoku D K, Espinosa J A. Intraoperative human vagus nerve compound action potentials. Acta Neurol Scand 110(2004): 232-238].

It is understood that although devices of the present invention may stimulate A and B nerve fibers, in practice they may also be used so as not to stimulate the largest A fibers (A-delta) and B fibers. In particular, if the stimulator amplitude has been increased to the point at which unwanted side effects begin to occur, the operator of the device may simply reduce the amplitude to avoid those effects. For example, vagal efferent fibers responsible for bronchoconstriction have been observed to have conduction velocities in the range of those of B fibers. In those experiments, bronchoconstriction was only produced when B fibers were activated, and became maximal before C fibers had been recruited [R. M. McALLEN and K. M. Spyer. Two types of vagal preganglionic motoneurones projecting to the heart and lungs. J. Physiol. 282(1978): 353-364]. Because proper stimulation with the disclosed devices does not result in the side-effect of bronchoconstriction, evidently the bronchoconstrictive B-fibers are possibly not being activated when the amplitude is properly set. Also, the absence of bradycardia or prolongation of PR interval suggests that cardiac efferent B-fibers are not stimulated. Similarly, A-delta afferents may behave physiologically like C fibers. Because stimulation with the disclosed devices does not produce nociceptive effects that would be produced by jugular A-delta fibers or C fibers, evidently the A-delta fibers may not be stimulated when the amplitude is properly set.

Figure 9:
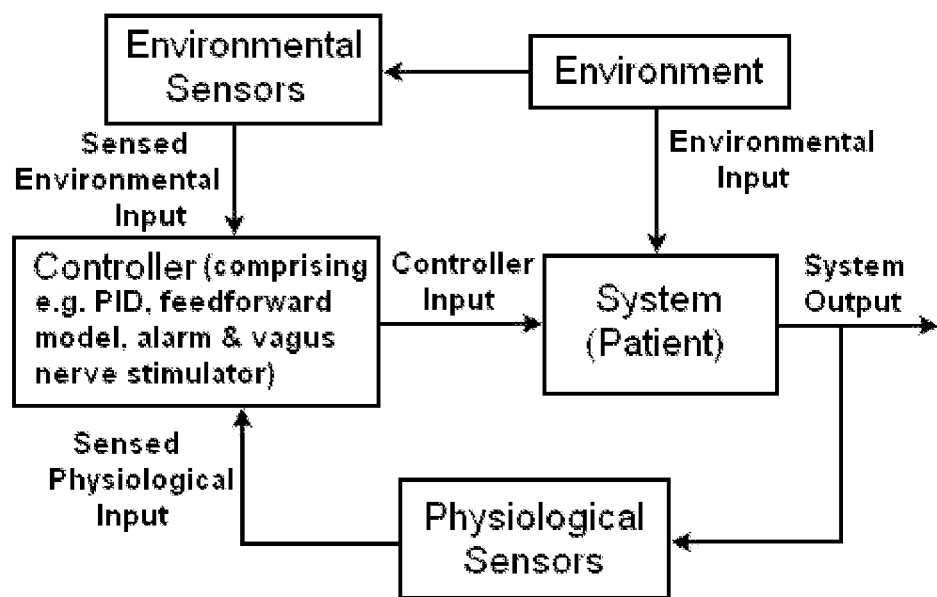
FIG. 9 illustrates connections between the controller and controlled system according to the present invention, their input and output signals, and external signals from the environment.
Figure 10:
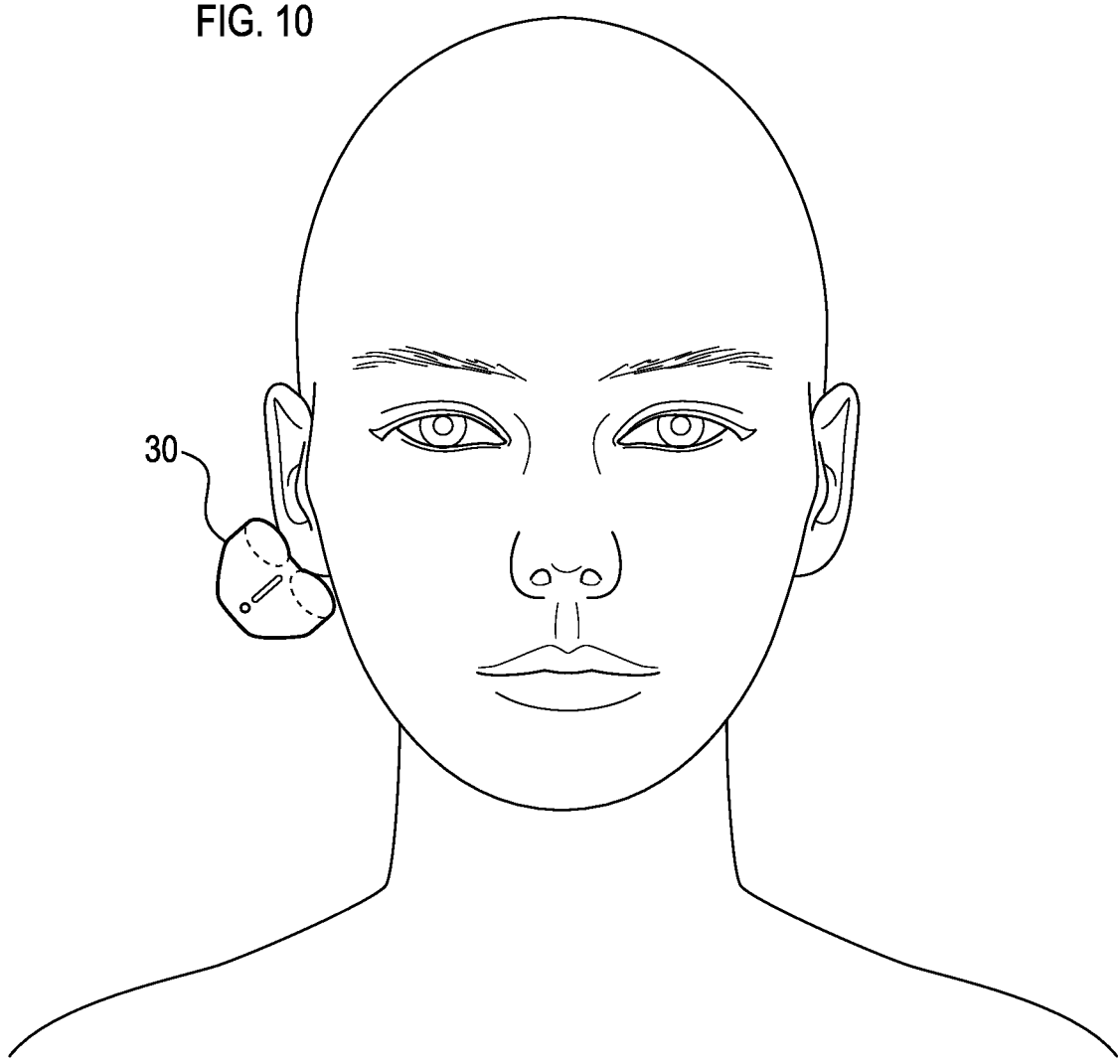
FIG. 10 illustrates the approximate position of the housing of the stimulator when used to stimulate an auricular branch of the vagus nerve of a patient.

The use of feedback to generate the modulation signal 400 may result in a signal that is not periodic, particularly if the feedback is produced from sensors that measure naturally occurring, time-varying aperiodic physiological signals from the patient (see FIG. 9). In fact, the absence of significant fluctuation in naturally occurring physiological signals from a patient is ordinarily considered to be an indication that the patient is in ill health. This is because a pathological control system that regulates the patient's physiological variables may have become trapped around only one of two or more possible steady states and is therefore unable to respond normally to external and internal stresses. Accordingly, even if feedback is not used to generate the modulation signal 400, it may be useful to artificially modulate the signal in an aperiodic fashion, in such a way as to simulate fluctuations that would occur naturally in a healthy individual. Thus, the noisy modulation of the stimulation signal may cause a pathological physiological control system to be reset or undergo a non-linear phase transition, through a mechanism known as stochastic resonance [B. SUKI, A. Alencar, M. K. Sujeer, K. R. Lutchen, J. J. Collins, J. S. Andrade, E. P. Ingenito, S. Zapperi, H. E. Stanley, Life-support system benefits from noise, Nature 393 (1998) 127-128; W Alan C MUTCH, M Ruth Graham, Linda G Girling and John F Brewster. Fractal ventilation enhances respiratory sinus arrhythmia. Respiratory Research 2005, 6:41, pp. 1-9].

So, in one embodiment of the present invention, the modulation signal 400, with or without feedback, will stimulate the selected nerve fibers in such a way that one or more of the stimulation parameters (power, frequency, and others mentioned herein) are varied by sampling a statistical distribution having a mean corresponding to a selected, or to a most recent running-averaged value of the parameter, and then setting the value of the parameter to the randomly sampled value. The sampled statistical distributions will comprise Gaussian and 1/f, obtained from recorded naturally occurring random time series or by calculated formula. Parameter values will be so changed periodically, or at time intervals that are themselves selected randomly by sampling another statistical distribution, having a selected mean and coefficient of variation, where the sampled distributions comprise Gaussian and exponential, obtained from recorded naturally occurring random time series or by calculated formula.

In another embodiment, devices in accordance with the present invention are provided in a "pacemaker" type form, in which electrical impulses 410 are generated to a selected region of the nerve by a stimulator device on an intermittent basis, to create in the patient a lower reactivity of the nerve.

Embodiments of the Electrode-Based Stimulator

The electrodes of the invention are applied to the surface of the neck, or to some other surface of the body, and are used to deliver electrical energy non-invasively to a nerve. The vagus nerve has been stimulated previously non-invasively using electrodes applied via leads to the surface of the skin. It has also been stimulated non-electrically through the use of mechanical vibration [HUSTON JM, Gallowitsch-Puerta M, Ochani M, Ochani K, Yuan R, Rosas-Ballina M et al (2007). Transcutaneous vagus nerve stimulation reduces serum high mobility group box 1 levels and improves survival in murine sepsis. Crit Care Med 35: 2762-2768; GEORGE M S, Aston-Jones G. Noninvasive techniques for probing neurocircuitry and treating illness: vagus nerve stimulation (VNS), transcranial magnetic stimulation (TMS) and transcranial direct current stimulation (tDCS). Neuropsychopharmacology 35(1,2010):301-316]. However, no such reported uses of noninvasive vagus nerve stimulation were directed to the treatment of headache sufferers. Patent No. U.S. Pat. No. 7,340,299, entitled Methods of indirectly stimulating the vagus nerve to achieve controlled asystole, to John D. PUSKAS, discloses the stimulation of the vagus nerve using electrodes placed on the neck of the patient, but that patent is unrelated to the treatment of headache sufferers. Non-invasive electrical stimulation of the vagus nerve has also been described in Japanese patent application JP2009233024A with a filing date of Mar. 26, 2008, entitled Vagus Nerve Stimulation System, to Fukui YOSHIHOTO, in which a body surface electrode is applied to the neck to stimulate the vagus nerve electrically. However, that application pertains to the control of heart rate and is unrelated to the treatment of headache sufferers. In patent publication US20080208266, entitled System and method for treating nausea and vomiting by vagus nerve stimulation, to LESSER et al., electrodes are used to stimulate the vagus nerve in the neck to reduce nausea and vomiting, but this too is unrelated to the treatment of headache sufferers.

Patent application US2010/0057154, entitled Device and method for the transdermal stimulation of a nerve of the human body, to DIETRICH et al., discloses a non-invasive transcutaneous/transdermal method for stimulating the vagus nerve, at an anatomical location where the vagus nerve has paths in the skin of the external auditory canal. Their non-invasive method involves performing electrical stimulation at that location, using surface stimulators that are similar to those used for peripheral nerve and muscle stimulation for treatment of pain (transdermal electrical nerve stimulation), muscle training (electrical muscle stimulation) and electroacupuncture of defined meridian points. The method used in that application is similar to the ones used in U.S. Pat. No. 4,319,584, entitled Electrical pulse acupressure system, to McCALL, for electroacupuncture; U.S. Pat. No. 5,514,175 entitled Auricular electrical stimulator, to KIM et al., for the treatment of pain; and U.S. Pat. No. 4,966,164, entitled Combined sound generating device and electrical acupuncture device and method for using the same, to COLSEN et al., for combined sound/electroacupuncture. A related application is US2006/0122675, entitled Stimulator for auricular branch of vagus nerve, to LIBBUS et al. Similarly, Patent No. U.S. Pat. No. 7,386,347, entitled Electric stimulator for alpha-wave derivation, to CHUNG et al., described electrical stimulation of the vagus nerve at the ear. Patent application US2008/0288016, entitled Systems and Methods for Stimulating Neural Targets, to AMURTHUR et al., also discloses electrical stimulation of the vagus nerve at the ear. U.S. Pat. No. 4,865,048, entitled Method and apparatus for drug free neurostimulation, to ECKERSON, teaches electrical stimulation of a branch of the vagus nerve behind the ear on the mastoid processes, in order to treat symptoms of drug withdrawal. KRAUS et al described similar methods of stimulation at the ear [KRAUS T, Hosl K, Kiess O, Schanze A, Kornhuber J, Forster C (2007). BOLD fMRI deactivation of limbic and temporal brain structures and mood enhancing effect by transcutaneous vagus nerve stimulation. J Neural Transm 114: 1485-1493]. However, none of the disclosures in these patents or patent applications for electrical stimulation of the vagus nerve at the ear are used to treat headache sufferers.

Embodiments of the present invention may differ with regard to the number of electrodes that are used, the distance between electrodes, and whether disk or ring electrodes are used. In preferred embodiments of the method, one selects the electrode configuration for individual patients, in such a way as to optimally focus electric fields and currents onto the selected nerve, without generating excessive currents on the surface of the skin. This tradeoff between focality and surface currents is described by DATTA et al. [Abhishek DATTA, Maged Elwassif, Fortunato Battaglia and Marom Bikson. Transcranial current stimulation focality using disc and ring electrode configurations: FEM analysis. J. Neural Eng. 5 (2008): 163-174]. Although DATTA et al. are addressing the selection of electrode configuration specifically for transcranial current stimulation, the principles that they describe are applicable to peripheral nerves as well [RATTAY F. Analysis of models for extracellular fiber stimulation. IEEE Trans. Biomed. Eng. 36 (1989): 676-682].

A preferred embodiment of an electrode-based stimulator is shown in FIG. 3. As shown, the stimulator (30) comprises two heads (31) and a connecting part that joins them. Each head (31) contains a stimulating electrode. The connecting part of the stimulator contains the electronic components and battery (not shown) that are used to generate the signals that drive the electrodes. However, in other embodiments of the invention, the electronic components that generate the signals that are applied to the electrodes may be separate, but connected to the electrode head (31) using wires or wireless communication with the heads. Furthermore, other embodiments of the invention may contain a single such head or more than two heads.

Heads of the stimulator (31) are applied to a surface of the patient's body, during which time the stimulator may be held in place by straps or frames or collars, or the stimulator may be held against the patient's body by hand. In either case, the level of stimulation power may be adjusted with a wheel (34) that also serves as an on/off switch. A light (35) is illuminated when power is being supplied to the stimulator. An optional cap may be provided to cover each of the stimulator heads (31), to protect the device when not in use, to avoid accidental stimulation, and to prevent material within the head from leaking or drying. Thus, in this embodiment of the invention, mechanical and electronic components of the stimulator (impulse generator, control unit, and power source) are compact, portable, and simple to operate.

Details of preferred embodiments of the stimulator heads are described in co-pending, commonly assigned applications that were cited above, the complete disclosures of which have been previously incorporated by reference for all purposes. As described in those applications, the stimulator designs situate the electrodes of the stimulator (340 in FIG. 1) remotely from the surface of the skin within a chamber, with conducting material (350 in FIG. 1) placed in a chamber between the electrode and the exterior component of the stimulator head that contacts the skin (351 in FIG. 1). One of the novelties of this design is that the stimulator, along with a correspondingly suitable stimulation waveform (see FIG. 2), shapes the electric field, producing a selective physiological response by stimulating that nerve, but avoiding substantial stimulation of nerves and tissue other than the target nerve, particularly avoiding the stimulation of nerves that produce pain. The shaping of the electric field is described in terms of the corresponding field equations in co-pending, commonly assigned application US20110230938 (application Ser. No. 13/075,746), entitled Devices and methods for non-invasive electrical stimulation and their use for vagal nerve stimulation on the neck of a patient, to SIMON et al., which is hereby incorporated by reference.

In one embodiment of the present invention, significant portions of the control of the vagus nerve stimulation reside in controller components that are physically separate from the housing of the stimulator. In this embodiment, separate components of the controller and stimulator housing may generally communicate with one another wirelessly. Thus, the use of wireless technology avoids the inconvenience and distance limitations of interconnecting cables. Additional reasons in the present disclosure for physically separating many components of the controller from the stimulator housing are as follows.

First, the stimulator may be constructed with the minimum number of components needed to generate the stimulation pulses, with the remaining components placed in parts of the controller that reside outside the stimulator housing, resulting in a lighter and smaller stimulator housing. In fact, the stimulator housing may be made so small that it could be difficult to place, on the stimulator housing's exterior, switches and knobs that are large enough to be operated easily.

Second, the controller (330 in FIG. 1) may be given additional functions when free from the limitation of being situated within or near the stimulator housing. For example, one may add to the controller a data logging component that records when and how stimulation has been applied to the patient, for purposes of medical recordkeeping and billing. The complete electronic medical record database for the patient may be located far from the stimulator (e.g., somewhere on the internet), and the billing system for the stimulation services that are provided may also be elsewhere, so it would be useful to integrate the controller into that recordkeeping and billing system, using a communication system that includes access to the internet or telephone networks.

Third, communication from the databases to the controller would also be useful for purposes of metering electrical stimulation of the patient, when the stimulation is self-administered. For example, if the prescription for the patient only permits only a specified amount of stimulation energy to be delivered during a single session of vagus nerve stimulation, followed by a wait-time before allowing the next stimulation, the controller can query the database and then permit the stimulation only when the prescribed wait-time has passed. Similarly, the controller can query the billing system to assure that the patient's account is in order, and withhold the stimulation if there is a problem with the account.

Fourth, as a corollary of the previous considerations, the controller may be constructed to include a computer program app (e.g, in a laptop computer or in a mobile phone or tablet), in which the databases are accessed via cell phone or internet connections. In such an application involving a mobile phone, in one embodiment, the phone could be connected to the stimulator housing or other system component using the phone's dock connector using a cable. In another embodiment, communication between the stimulator housing and mobile phone could be wireless. In yet another embodiment, communication between the stimulator housing and mobile phone may be via a stimulator docking station that communications with both the stimulator housing and mobile phone.

Fifth, in some applications, it is essential that the stimulator housing and parts of the controller be physically separate. For example, when the patient is a child, one wants to make it impossible for the child to control or adjust the vagus nerve stimulation. The best arrangement in that case is for the stimulator housing to have no control switches or adjustment knobs that could be touched by the child. Alternatively, any switches and knobs on the stimulator head can be disabled, and control of the stimulation then resides only in a remote controller (typically handheld) with a child-proof operation, which would be kept the possession of a parent.

Sixth, in some applications, the particular control signal that is transmitted to the stimulator housing by the controller will depend on physiological and environmental signals that are themselves transmitted to and analyzed by the controller. For example, the stimulator head may incorporate one or more accelerometers, which can be used to detect movement of the stimulator housing relative to the vagus nerve, wherein the detected movement can be used to automatically modulate of the amplitude of the stimulation. In such applications, many of the physiological and environmental signals may already be transmitted wirelessly, in which case it is most convenient to design an external part of the controller as the hub of all such wireless activity, including any wireless signals that are sent to and from the stimulator housing.

With these considerations in mind, a preferred embodiment of the invention includes a docking station (40 in FIG. 3C) that may be used as a recharging power supply for the stimulator housing (30 in FIG. 3), may send/receive data to/from the stimulator housing, and may send/receive data to/from databases and other components of the system, including those that are accessible via the internet. Thus, prior to any particular stimulation session, the docking station may load into the stimulator parameters of the session, including waveform parameters See FIG. 2 and below for criteria used to select the parameters. In a preferred embodiment, the docking station also limits the amount of stimulation energy that may be consumed by the patient in the session by charging the stimulator's rechargable battery with only a specified amount of releasable electrical energy, which is different than setting a parameter to restrict the duration of a stimulation session. As a practical matter, the stimulator may therefore use two batteries, one for stimulating the patient (the charge of which may be limited by the docking station) and the other for performing other functions such as data transmission. Methods for evaluating a battery's charge or releasable energy are known in the art, for example, in U.S. Pat. No. 7,751,891, entitled Power supply monitoring for an implantable device, to ARMSTRONG et al. Alternatively, control components within the stimulator housing may monitor the amount of stimulation energy that has been consumed during a stimulation session and stop the stimulation session when a limit has been reached, irrespective of the time when the limit has been reached.

The docking station is shown as item 40 in FIG. 3. The stimulator housing 30 and docking station 40 can be connected to one another by inserting the connector 36 near the center of the base 38 of the stimulator housing 30 into a mated connector 42 of the docking station 40. As shown in FIG. 3, the docking station 30 has an indentation or aperture 41 that allows the base 38 of the stimulator housing 30 to be seated securely into the docking station. The connector 36 of the stimulator housing is recessed in an aperture 37 of the base of the stimulator housing 30 that may be covered by a detachable or hinged cover when the stimulator housing is not attached to the docking station (not shown).

The mated connectors 36 and 42 have a set of contacts that have specific functions for the transfer of power to charge a rechargable battery in the stimulator housing 30 and to transfer data bidirectionally between the stimulator housing and docking station. As a safety feature, the contacts at the two ends of the mated connector are connected to one another within the stimulator housing and within the docking station, such that if physical connection is not made at those end contacts, all the other contacts are disabled via active switches. Also, the connectors 36 and 42 are offset from the center of the base 38 of the stimulator housing 30 and from the center of the indentation or aperture 41 of the docking station 40, so that the stimulator housing can be inserted in only one way into the docking station. That is to say, when the stimulator housing 30 is attached to the docking station 40, the front of the stimulator housing 30 must be on the front side of the docking station 40. As shown, the back side of the docking station has an on/off switch 44 and a power cord 43 that attaches to a wall outlet. The docking station 40 also has ports (e.g., USB ports) for connecting to other devices, one of which 45 is shown on the side of the station, and others of which are located on the front of the station (not shown). The front of the docking station has colored lights to indicate whether the docking station has not (red) or has (green) charged the stimulator so as to be ready for a stimulation session.

Through cables to the communication port 45, the docking station 40 can communicate with the different types of devices, such as those illustrated in FIG. 4. Handheld devices may resemble conventional remote controls with a display screen (FIG. 4A) or mobile phones (FIG. 4B). Other type of devices with which the docking station may communicate are touchscreen devices (FIG. 4C) and laptop computers (FIG. 4D).

Figure 5:
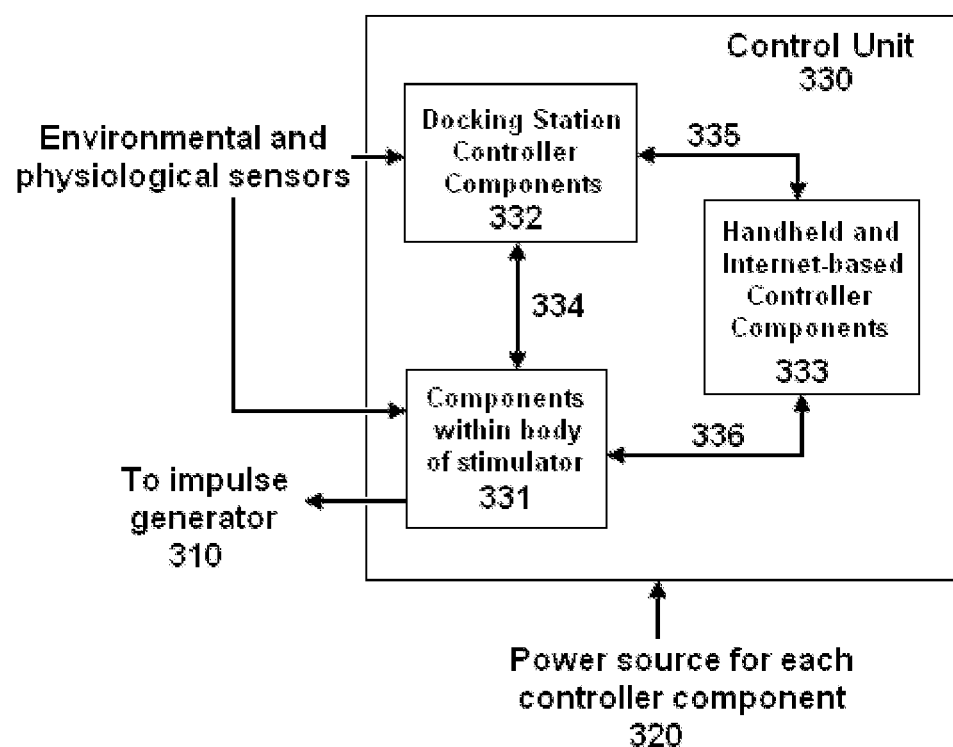
FIG. 5 shows an expanded block diagram of the control unit shown in FIG. 1, separating components of the control unit into those within the body of the stimulator, those within the docking station, and those within hand-held and internet-based devices, also showing communication paths between such components.

The communication connections between different components of the stimulator's controller are shown in FIG. 5, which is an expanded representation of the control unit 330 in FIG. 1. Connection between the docking station controller components 332 and components within the stimulator housing 331 is denoted in FIG. 5 as 334. For example, that connection is made when the stimulator housing is connected to the docking station as described above. Connection between the docking station controller components 332 and devices 333 such as those shown in FIG. 4 (generally internet-based components) is denoted as 335. Connection between the components within the stimulator housing 331 and devices 333 such as those shown in FIG. 4 (generally internet-based components) is denoted as 336. Different embodiments of the invention may lack one or more of the connections. For example, if the connection between the stimulator housing and the devices 333 is only through the docking station controller components, then in that embodiment of the invention, only connections 334 and 335 would be present.

The connections 334, 335 and 336 in FIG. 5 may be wired or wireless. For example, if the controller component 333 is the mobile phone shown in FIG. 4B, the connection 335 to a docking station port (45 in FIG. 3) could be made with a cable to the phone's own docking port. Similarly, if the controller component 333 is the laptop computer shown in FIG. 4D, the connection 335 to a docking station port (45 in FIG. 3) could be made with a cable to a USB port on the computer. Alternatively, the docking station 40 may contain the necessary computer elements to connect the stimulator directly to the internet for web-based delivery of the therapy to the patient (i.e., without external devices 333 such as shown in FIG. 4).

Although infrared or ultrasound wireless control might be used to communicate between components of the controller, they are not preferred because of line-of-sight limitations. Instead, in the present disclosure, the communication between devices preferably makes use of radio communication within unlicensed ISM frequency bands (260-470 MHz, 902-928 MHz, 2400-2.4835 GHz). Components of the radio frequency system in devices in 331, 332, and 333 typically comprise a system-on-chip transciever with an integrated microcontroller; a crystal; associated balun & matching circuitry, and an antenna [Dag GRINI. RF Basics, RF for Non-RF Engineers. Texas Instruments, Post Office Box 655303, Dallas, Tex. 75265, 2006].

Transceivers based on 2.4 GHz offer high data rates (greater than 1 Mbps) and a smaller antenna than those operating at lower frequencies, which makes them suitable for with short-range devices. Furthermore, a 2.4 GHz wireless standard (Bluetooth, Wi-Fi, and ZigBee) may be used as the protocol for transmission between devices. Although the ZigBee wireless standard operates at 2.4 GHz in most jurisdictions worldwide, it also operates in the ISM frequencies 868 MHz in Europe, and 915 MHz in the USA and Australia. Data transmission rates vary from 20 to 250 kilobits/second with that standard. Because many commercially available health-related sensors may operate using ZigBee, its use may be recommended for applications in which the controller uses feedback and feedforward methods to adjust the patient's vagus nerve stimulation based on the sensors' values, as described below in connection with FIG. 9 [ZigBee Wireless Sensor Applications for Health, Wellness and Fitness. ZigBee Alliance 2400 Camino Ramon Suite 375 San Ramon, Calif. 94583].

A 2.4 GHz radio has higher power consumption than radios operating at lower frequencies, due to reduced circuit efficiencies. Furthermore, the 2.4 GHz spectrum is crowded and subject to significant interference from microwave ovens, cordless phones, 802.11b/g wireless local area networks, Bluetooth devices, etc. Sub-GHz radios enable lower power consumption and can operate for years on a single battery. These factors, combined with lower system cost, make sub-GHz transceivers ideal for low data rate applications that need maximum range and multi-year operating life.

The antenna length needed for operating at different frequencies is 17.3 cm at 433 MHz, 8.2 cm at 915 MHz, and 3 cm at 2.4 GHz. Therefore, unless the antenna is included in a neck collar that supports the device shown in FIG. 3A, the antenna length may be a disadvantage for 433 MHz transmission. The 2.4 GHz band has the advantage of enabling one device to serve in all major markets worldwide since the 2.4 GHz band is a global spectrum. However, 433 MHz is a viable alternative to 2.4 GHz for most of the world, and designs based on 868 and 915 MHz radios can serve the US and European markets with a single product.

Range is determined by the sensitivity of the transceiver and its output power. A primary factor affecting radio sensitivity is the data rate. Higher data rates reduce sensitivity, leading to a need for higher output power to achieve sufficient range. For many applications that require only a low data rate, the preferred rate is 40 Kbps where the transceiver can still use a standard off-the-shelf 20 parts per million crystal.

Figure 2B:
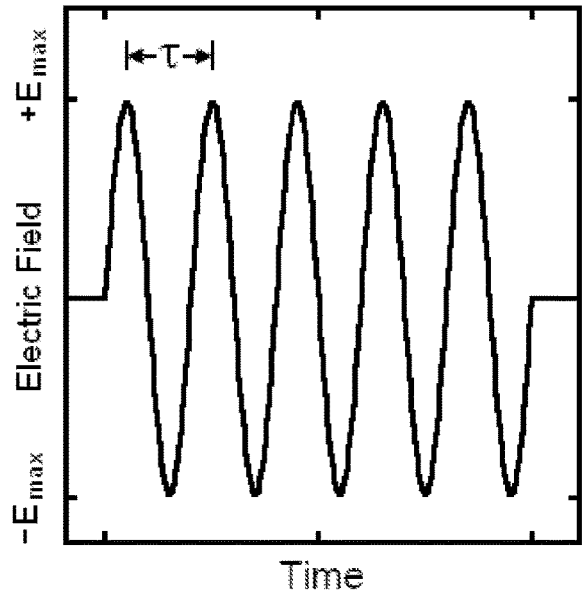
FIG. 2B illustrates an exemplary electrical waveform for stimulating and/or modulating impulses that are applied to a nerve according to the present invention.
Figure 2C:
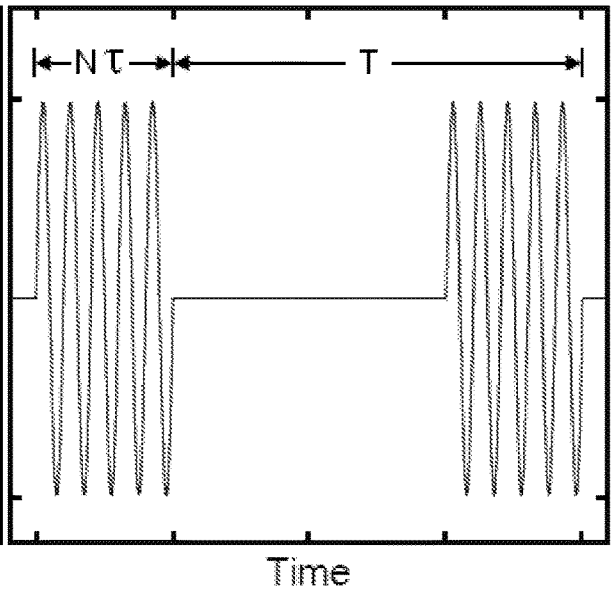
FIG. 2C illustrates an exemplary electrical waveform for stimulating and/or modulating impulses that are applied to a nerve according to the present invention
Figure 4A:
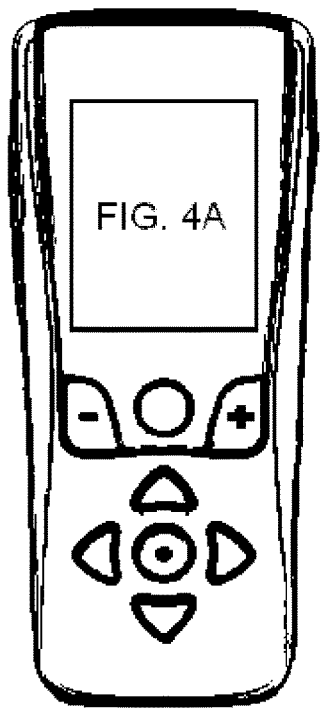
FIG. 4A illustrates a remote control device for communicating with the docking station of FIG. 3C.
Figure 4B:
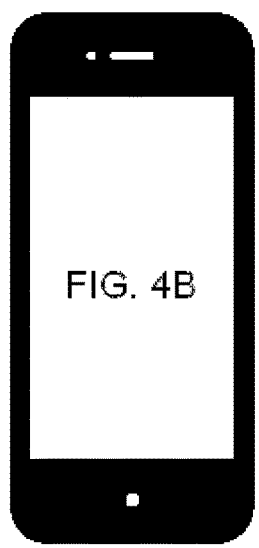
FIG. 4B illustrates a mobile phone for communicating with the docking station of FIG. 3C.
Figure 4C:
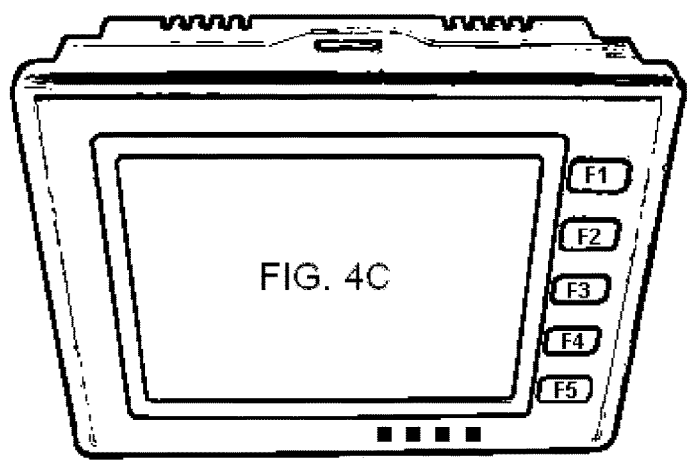
FIG. 4C illustrates a touchscreen device for communicating with the docking station of FIG. 3C.
Figure 4D:
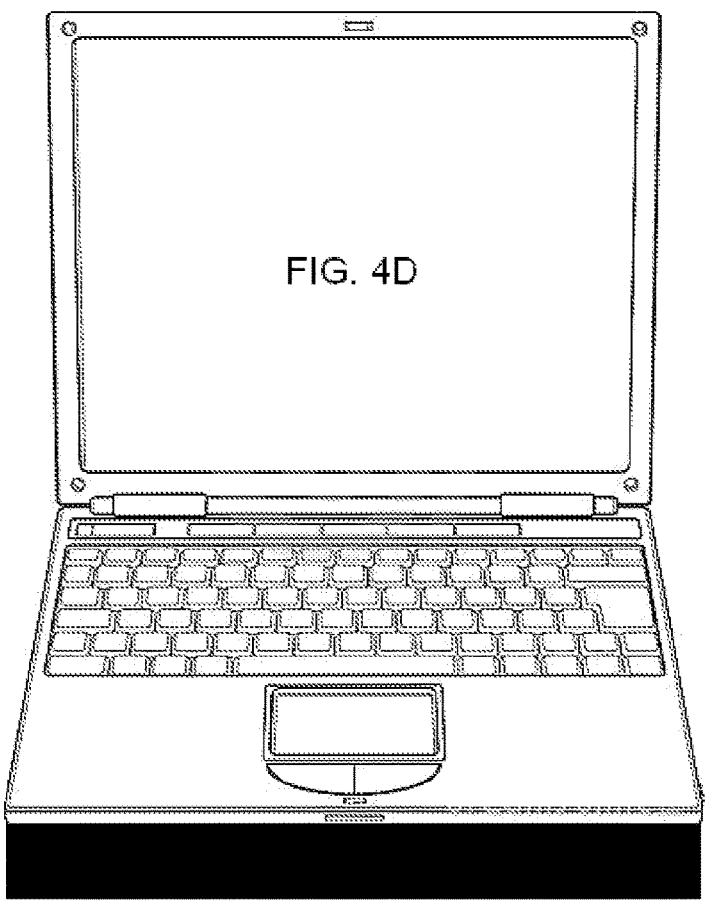
FIG. 4D illustrates a laptop computer for communicating with the docking station of FIG. 3C.

A typical signal waveform that might be transmitted wirelessly to the stimulator housing (31 in FIG. 3) was shown in FIGS. 2B and 2C. As seen there, individual sinusoidal pulses have a period of tau, and a burst consists of N such pulses. This is followed by a period with no signal (the inter-burst period). The pattern of a burst followed by silent inter-burst period repeats itself with a period of T. For example, the sinusoidal period tau may be 200 microseconds; the number of pulses per burst may be N=5; and the whole pattern of burst followed by silent inter-burst period may have a period of T=40000 microseconds, which is comparable to 25 Hz stimulation (a much smaller value of T is shown in FIG. 2C to make the bursts discernable). When these exemplary values are used for T and tau, the waveform contains significant Fourier components at higher frequencies (1/200 microseconds=5000/sec). Such a signal may be easily transmitted using 40 Kbps radio transmission. Compression of the signal is also possible, by transmitting only the signal parameters tau, N, T, Emax, etc., but in that case the stimulator housing's control electronics would then have to construct the waveform from the transmitted parameters, which would add to the complexity of components of the stimulator housing (31 in FIG. 3).

However, because it is contemplated that sensors attached to the stimulator housing may also be transmitting information, such as accelerometers that are used to detect motion of the stimulator relative to the vagus nerve, the data transfer requirements may be substantially greater than what is required only to transmit the signal shown in FIG. 2. Therefore, the present invention may make use of any frequency band, not limited to the ISM frequency bands, as well as techniques known in the art to suppress or avoid noise and interferences in radio transmission, such as frequency hopping and direct sequence spread spectrum.

Application of the Stimulators to the Neck of the Patient

Selected nerve fibers are stimulated in different embodiments of methods that make use of the disclosed electrical stimulation devices, including stimulation of the vagus nerve at a location in the patient's neck. At that location, the vagus nerve is situated within the carotid sheath, near the carotid artery and the interior jugular vein. The carotid sheath is located at the lateral boundary of the retropharyngeal space on each side of the neck and deep to the sternocleidomastoid muscle. The left vagus nerve is sometimes selected for stimulation because stimulation of the right vagus nerve may produce undesired effects on the heart, but depending on the application, the right vagus nerve or both right and left vagus nerves may be stimulated instead.

The three major structures within the carotid sheath are the common carotid artery, the internal jugular vein and the vagus nerve. The carotid artery lies medial to the internal jugular vein, and the vagus nerve is situated posteriorly between the two vessels. Typically, the location of the carotid sheath or interior jugular vein in a patient (and therefore the location of the vagus nerve) will be ascertained in any manner known in the art, e.g., by feel or ultrasound imaging. Proceeding from the skin of the neck above the sternocleidomastoid muscle to the vagus nerve, a line may pass successively through the sternocleidomastoid muscle, the carotid sheath and the internal jugular vein, unless the position on the skin is immediately to either side of the external jugular vein. In the latter case, the line may pass successively through only the sternocleidomastoid muscle and the carotid sheath before encountering the vagus nerve, missing the interior jugular vein. Accordingly, a point on the neck adjacent to the external jugular vein might be preferred for non-invasive stimulation of the vagus nerve. The magnetic stimulator coil may be centered on such a point, at the level of about the fifth to sixth cervical vertebra.

Figure 6:
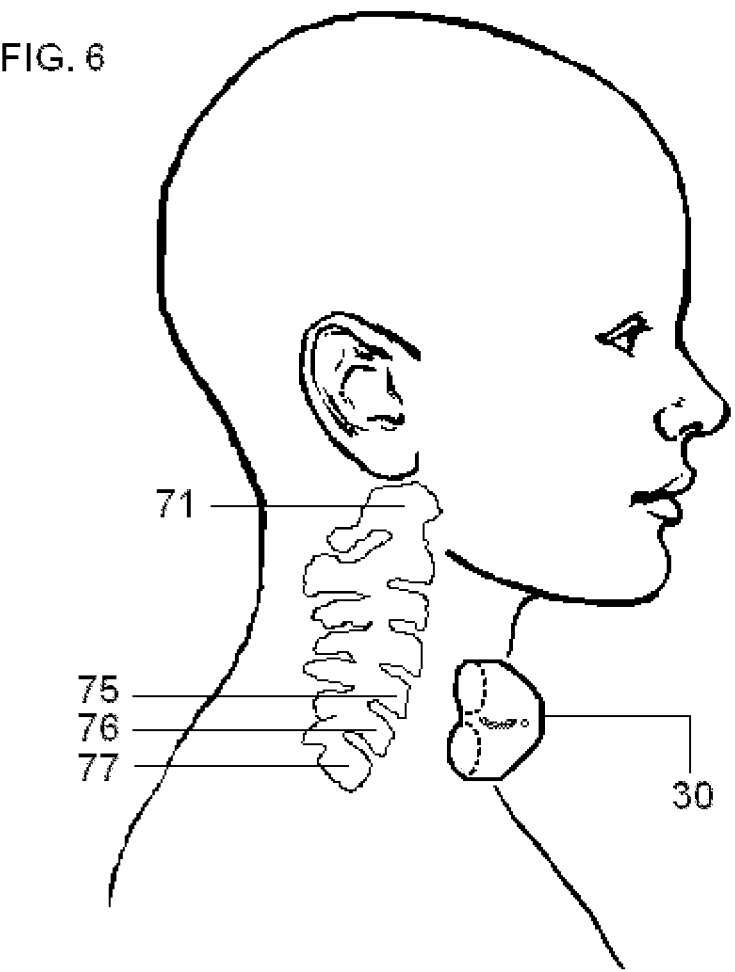
FIG. 6 illustrates the approximate position of the housing of the stimulator according to one embodiment of the present invention, when used to stimulate the right vagus nerve in the neck of an adult patient.
Figure 7:
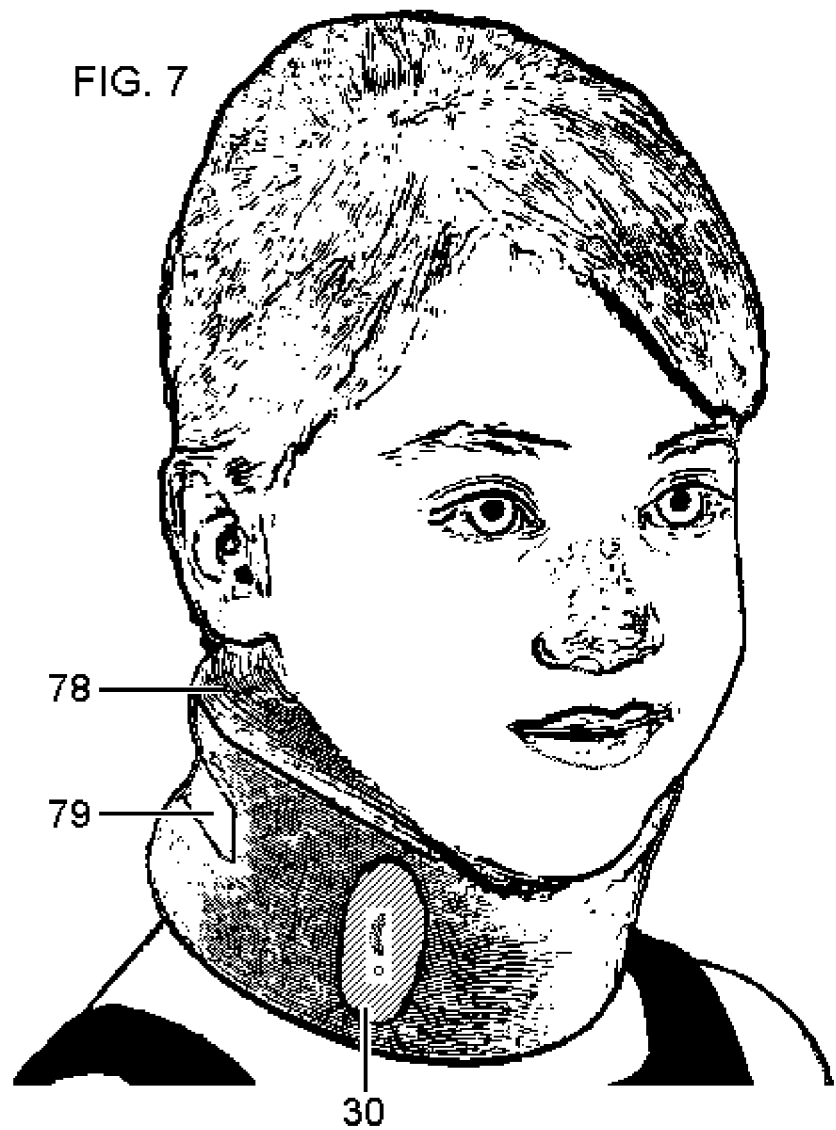
FIG. 7 illustrates the approximate position of the housing of the stimulator according one embodiment of the present invention, when used to stimulate the right vagus nerve in the neck of a child.

FIG. 6 illustrates use of the device 30 shown in FIG. 3 to stimulate the vagus nerve at that location in the neck, in which the stimulator device 30 is shown to be applied to the target location on the patient's neck as described above. For reference, FIG. 6 shows the locations of the following vertebrae: first cervical vertebra 71, the fifth cervical vertebra 75, the sixth cervical vertebra 76, and the seventh cervical vertebra 77. FIG. 7 shows the stimulator 30 applied to the neck of a child, which is partially immobilized with a foam cervical collar 78 that is similar to ones used for neck injuries and neck pain. The collar is tightened with a strap 79, and the stimulator is inserted through a hole in the collar to reach the child's neck surface. As shown, the stimulator is turned on and off with a control knob, and the amplitude of stimulation may also be adjusted with the control knob that is located on the stimulator. In other models, the control knob is absent or disabled, and the stimulator may be turned on and off remotely, using a wireless controller that may be used to adjust the stimulation parameters of the controller (e.g., on/off, stimulation amplitude, frequency, etc.).

Figure 8:
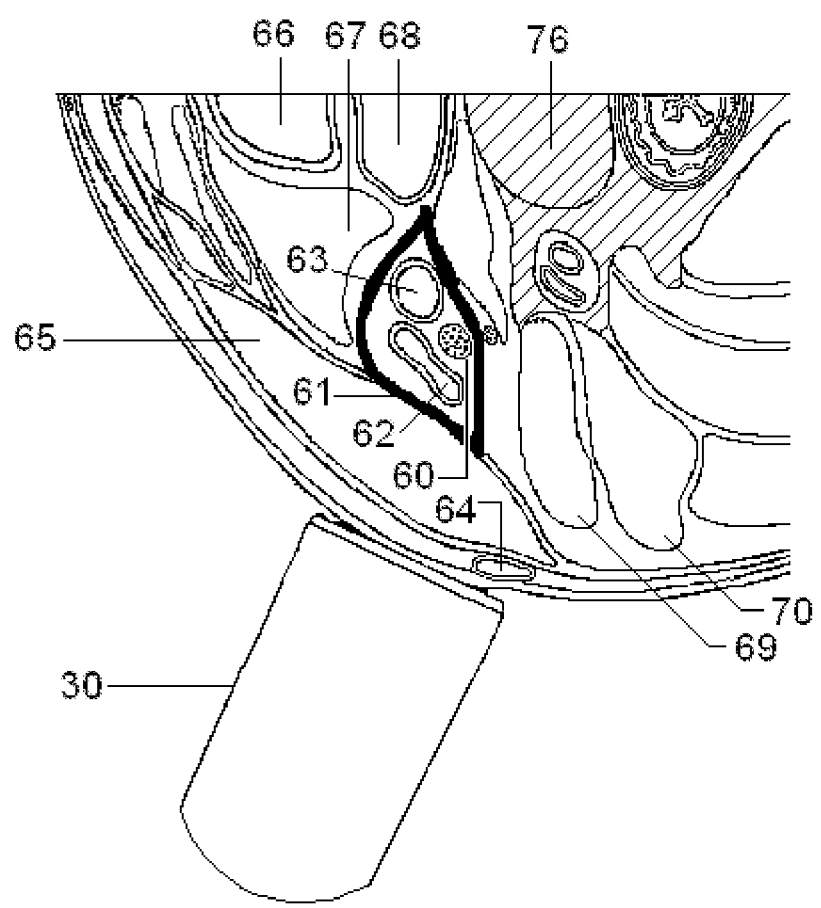
FIG. 8 illustrates the housing of the stimulator according one embodiment of the present invention, when positioned to stimulate a vagus nerve in the patient's neck, wherein the stimulator is applied to the surface of the neck in the vicinity of the identified anatomical structures.

FIG. 8 provides a more detailed view of use of the electrical stimulator 30, when positioned to stimulate the vagus nerve at the neck location that is indicated in FIG. 6. The vagus nerve 60 is identified in FIG. 8, along with the carotid sheath 61 that is identified there in bold peripheral outline. The carotid sheath encloses not only the vagus nerve, but also the internal jugular vein 62 and the common carotid artery 63. Features that may be identified near the surface of the neck include the external jugular vein 64 and the sternocleidomastoid muscle 65. Additional organs in the vicinity of the vagus nerve include the trachea 66, thyroid gland 67, esophagus 68, scalenus anterior muscle 69, and scalenus medius muscle 70. The sixth cervical vertebra 76 is also shown in FIG. 8, with bony structure indicated by hatching marks.

Methods of treating a patient comprise stimulating the vagus nerve as indicated in FIGS. 6 and 7, using the electrical stimulation devices that are disclosed here. Stimulation may be performed on the left or right vagus nerve or on both of them simultaneously or alternately. The position and angular orientation of the device are adjusted about that location until the patient perceives stimulation when current is passed through the stimulator electrodes. The applied current is increased gradually, first to a level wherein the patient feels sensation from the stimulation. The power is then increased, but is set to a level that is less than one at which the patient first indicates any discomfort. Straps, harnesses, or frames may be used to maintain the stimulator in position. The stimulator signal may have a frequency and other parameters that are selected to produce a therapeutic result in the patient, i.e., stimulation parameters for each patient are adjusted on an individualized basis. Ordinarily, the amplitude of the stimulation signal is set to the maximum that is comfortable for the patient, and then the other stimulation parameters are adjusted.

The stimulation is then performed with a sinusoidal burst waveform like that shown in FIG. 2. As seen there, individual sinusoidal pulses have a period of $\tau$, and a burst consists of N such pulses. This is followed by a period with no signal (the inter-burst period). The pattern of a burst followed by silent inter-burst period repeats itself with a period of T. For example, the sinusoidal period $\tau$ may be between about 50-1000 microseconds (equivalent to about 1-20 KHz), preferably between about 100-400 microseconds (equivalent to about 2.5-10 KHz), more preferably about 133-400 microseconds (equivalent to about 2.5-7.5 KHZ) and even more preferably about 200 microseconds (equivalent to about 5 KHz); the number of pulses per burst may be N=1-20, preferably about 2-10 and more preferably about 5; and the whole pattern of burst followed by silent inter-burst period may have a period T comparable to about 10-100 Hz, preferably about 15-50 Hz, more preferably about 25-35 Hz and even more preferably about 25 Hz (a much smaller value of T is shown in FIG. 2E to make the bursts discernable). When these exemplary values are used for T and $\tau$, the waveform contains significant Fourier components at higher frequencies (1/200 microseconds=5000/sec), as compared with those contained in transcutaneous nerve stimulation waveforms, as currently practiced.

When a patient is using the stimulation device to perform self-stimulation therapy, e.g., at home or at a workplace, he or she will follow the steps that are now described. In the following description, it is assumed that the stimulator (30 in FIG. 3) has been placed in the docking station (40 in FIG. 3), where it would ordinarily be placed between stimulation sessions for protection and safekeeping. The previous stimulation session will ordinarily have discharged the rechargeable batteries of the stimulator housing, and between sessions, the docking station will have recharged the stimulator at most only up to a minimum level. If the stimulator's batteries had charge remaining from the previous stimulation session, the docking station will have discharged the stimulator to a minimum level that will not support stimulation of the patient.

The patient will then interact with the mated docking station and stimulator via one of the handheld or internet-based devices (333 in FIG. 5), to which the docking station can be connected wirelessly or through a cable. For example, the patient can initiate the stimulation session using a mobile phone (FIG. 4B) or laptop computer (FIG. 4D) by invoking a computer program (on the laptop computer or through an app on the mobile phone) that is designed to initiate use of the stimulator. For security reasons, the program would begin with the request for a user name and a password, and that user's demographic information and any data from previous stimulator experiences would already be associated with it in the login account. If the patient's physician has not authorized further treatments, the docking station will not charge the stimulator's batteries, and instead, the computer program will call or otherwise communicate with the physician's computer requesting authorization. After authorization by the physician is received, the computer program (on the laptop computer or through an app on the mobile phone) may also query a database that is ordinarily located somewhere on the internet to verify that the patient's account is in order. If it is not in order, the program may then request prepayment for one or more stimulation sessions, which would be paid by the patient using a credit card, debit card, PayPal or the like. The computer program will also query its internal database or that of the docking station to determine that sufficient time has elapsed between when the stimulator was last placed in the docking station and the present time, to verify that any required wait-time has elapsed.

Having received authorization to perform a nerve stimulation session, the patient interface computer program will then ask the patient questions that are relevant to the selection of parameters that the docking station will use to make the stimulator ready for the stimulation session. The questions that the computer program asks are dependent on the condition for which the patient is being treated, which for present purposes is considered to be treatment for a migraine headache. That headache may in principle be in any of the headache phases (prodrome, aura, headache pain, postdrome, and interictal period), which would be ascertained through the computer program's questions. The questions may be things like (1) is this an acute or prophylactic treatment? (2) if acute, then how severe is your headache, how long have you had it, (3) has anything unusual or noteworthy occurred since the last stimulation?, etc. In general, the types of posed questions are ones that would be placed in a headache diary [TASSORELLI C, Sances G, Allena M, Ghiotto N, Bendtsen L, Olesen J, Nappi G, Jensen R. The usefulness and applicability of a basic headache diary before first consultation: results of a pilot study conducted in two centres. Cephalalgia 28(10,2008):1023-1030].

Having received such preliminary information from the patient, the computer program will then send data to the docking station, giving it the instructions needed to perform instrument diagnostic tests of the stimulator and docking station and to make the stimulator ready for the stimulation session. In general, the algorithm for setting the stimulator parameters will have been decided by the physician and will include the extent to which the stimulator batteries should be charged, which the vagus nerve should be stimulated (right or left), and the time that the patient must wait after the stimulation session is ended until initiation of a subsequent stimulation session. The computer will query the physician's computer to ascertain whether there have been any updates to the algorithm, and if not, will use the existing algorithm. The patient will also be advised of the stimulation session parameter values by the interface computer program, so as to know what to expect.

Once the docking station has rapidly charged the stimulator's batteries to the requisite charge, a light will turn on (e.g., green) on the front of the docking station. At that point, the patient may remove the stimulator from the docking station to begin the vagus nerve stimulation, as shown in FIG. 6. Multiple methods may be used to test whether the patient is attempting to stimulate the vagus nerve on the intended side of the neck. A first method makes use of miniature three-axis accelerometers (possibly with combined gyroscopes) that are embedded in the body of the stimulator (for example, Model LSM330DL from STMicroelectronics, 750 Canyon Dr #300 Coppell, Tex. 75019). Such an accelerometer is situated in each of the two simulator heads (31 in FIG. 3), and another accelerometer is situated in the vicinity of the bottom of the stimulator (38 in FIG. 3). The accelerometers will be providing positional data even when the stimulator is attached to the docking station, so that the orientation of the stimulator with respect to gravity is known from that data, and initial positions of the accelerometers with respect to one another are also known from the structure of the stimulator. Inferences that may be made, as described below, may then be made by a computer program that is implemented by a microprocessor that is situated within the stimulator housing. The patient will be facing the docking station when he or she removes the stimulator from the docking station, thereby defining directions left and right as viewed by the patient. As the patient holds the stimulator in a hand and even walks about the room, relative positions of the stimulator heads retain their left and right aspects because the stimulator housing and patient with the stimulator in hand move together. Thus, by integrating the accelerations provided by the accelerometers to infer the present location of the accelerometers, the directions left and right may also be inferred, after translocation and rotation of the initial accelerometer axes into the present axes. So when the patient begins the stimulation as indicated by rotation of the amplitude thumbwheel (34 in FIG. 3), it may be determined that the stimulator heads with respect to the base of the stimulator are pointing generally in the leftward direction (i.e., right vagus nerve stimulated is being attempted) or generally in the rightward direction (i.e., left vagus nerve stimulation is being attempted).

The left versus right inference described in the previous paragraph may be confirmed by the stimulator's computer program, by examining the positions of the stimulator heads with respect to one another, as indicated by the accelerometer data. The stimulator shown in FIG. 3A has a thumbwheel that could be rotated by either the left or right hand thumbs. If the wheel is being rotated by the right hand thumb (right vagus nerve stimulated is being attempted), a particular stimulator head will be on top. However, if the wheel is being rotated by the left hand thumb (left vagus nerve stimulated is being attempted), the other stimulator head will be on top. Alternatively, the decision by the stimulator's computer program as to which hand is being used to hold the stimulator may be made by measuring capacitance on the outside of the stimulator body, which may distinguish fingers wrapped around the device versus the ball of a thumb [Raphael WIMMER and Sebastian Boring. HandSense: discriminating different ways of grasping and holding a tangible user interface. Proceedings of the 3rd International Conference on Tangible and Embedded Interaction, pp. 359-362. ACM New York, N.Y., 2009]. If the combined decision of the stimulator is that the patient is attempting to stimulate the wrong vagus nerve, the stimulation will be withheld, and the stimulator may then communicate with the patient via the interface computer program (in the mobile phone or laptop computer) to alert the patient of that fact and possibly allow for overriding that decision.

Assume now that the vagus nerve is being stimulated on the correct side of the neck. The patient will then adjust the position and angular orientation of the stimulator about what he or she thinks is the correct neck position, until he or she perceives stimulation when current is passed through the stimulator electrodes. The applied current is increased gradually, first to a level wherein the patient feels sensation from the stimulation. The stimulation amplitude is then increased by the patient, but is set to a level that is less than one at which he first senses any discomfort. By trial and error, the position of the stimulator is then optimized by the patient, who tries to find the greatest acceptable sensation with the lowest acceptable stimulation amplitude. If the stimulator is being held in place by hand, it is likely that there may be inadvertent fluctuating movement of the stimulator, due for example to neck movement during respiration. Such relative movements will affect the effectiveness of the stimulation. However, they may be monitored by accelerometers in the stimulator, which may be transmitted as movement data from the stimulator to the patient interface computer program (in the mobile phone or laptop computer). By watching a graphical display of the relative movements shown by the patient interface computer program, the patient may use that display in an attempt to deliberately minimize the movements. Otherwise, the patient may attempt to adjust the amplitude of the stimulator as compensation for movement of the stimulator away from its optimum position. In a section that follows, it is described how the stimulator itself may modulate the amplitude of the stimulation in order to make such compensations.

The stimulation waveform may be synthesized within the stimulator housing, or it may be synthesized in the docking station or some other component of the system and transmitted to the stimulator housing. Note that the latter is generally different than the transmission of a pre-recorded waveform signal [U.S. Pat. No. 8,112,154, entitled Systems and methods for neuromodulation using pre-recorded waveforms, to REZAI et al]. In either case, stimulation by the patient will then continue until the batteries of the stimulator are depleted, or the patient decides to terminate the stimulation session. At that point, the patient will insert the stimulator housing back into the docking station, whereupon the stimulator will transfer to the docking station data that its microprocessor has caused to be stored regarding the stimulation session (e.g., stimulation amplitude as a function of time and information about movements of the device during the session, duration of the stimulation, etc.). Such information will then be transmitted to and displayed by the patient interface computer program (in the mobile phone or laptop computer), which will subsequently ask the patient questions regarding the effectiveness of the stimulation. Such questions may be in regards to the post-stimulation severity of the headache, whether the severity decreased gradually or abruptly during the course of the stimulation, and whether anything unusual or noteworthy occurred during the stimulation. All such post-stimulation data will also be delivered over the internet by the patient interface computer program to the physician's computer for review and possible adjustment of the algorithm that is used to select stimulation parameters and regimens. It is understood that the physician will adjust the algorithm based not only on the experience of each individual patient, but on the experience of all patients collectively so as to improve effectiveness of the stimulator's use, for example, by identifying characteristics of most and least responsive patients.

Before logging off of the interface computer program, the patient may also review database records and summaries about all previous treatment sessions, so as to make his or her own judgment about treatment progress. If the stimulation was part of a prophylactic treatment regimen that was prescribed by the patient's physician, the patient interface computer program will remind the patient about the schedule for the upcoming self-treatment sessions and allow for a rescheduling if necessary.

For some patients, the stimulation may be performed for as little as five minutes, but it may also be for up to 30 minutes or longer. The treatment is generally performed once or twice daily or several times a week, for 12 weeks or longer before a decision is made as to whether to continue the treatment. For patients experiencing intermittent symptoms, the treatment may be performed only when the patient is symptomatic. However, it is understood that parameters of the stimulation protocol may be varied in response to heterogeneity in the pathophysiology of patients. Different stimulation parameters may also be used as the course of the patient's condition changes.

In some embodiments of the invention, pairing of vagus nerve stimulation may be with a additional sensory stimulation. The paired sensory stimulation may be bright light, sound, tactile stimulation, or electrical stimulation of the tongue to simulate odor/taste, e.g., pulsating with the same frequency as the vagus nerve electrical stimulation. The rationale for paired sensory stimulation is the same as simultaneous, paired stimulation of both left and right vagus nerves, namely, that the pair of signals interacting with one another in the brain may result in the formation of larger and more coherent neural ensembles than the neural ensembles associated with the individual signals, thereby enhancing the therapeutic effect. This pairing may be considered especially when some such corresponding sensory circuit of the brain is thought to be partly responsible for triggering the migraine headache.

Selection of stimulation parameters to preferentially stimulate particular regions of the brain may be done empirically, wherein a set of stimulation parameters are chosen, and the responsive region of the brain is measured using fMRI or a related imaging method [CHAE J H, Nahas Z, Lomarev M, Denslow S, Lorberbaum J P, Bohning D E, George M S. A review of functional neuroimaging studies of vagus nerve stimulation (VNS). J Psychiatr Res. 37(6,2003): 443-455; CONWAY C R, Sheline Y I, Chibnall J T, George M S, Fletcher J W, Mintun M A. Cerebral blood flow changes during vagus nerve stimulation for depression. Psychiatry Res. 146(2,2006):179-84]. Thus, by performing the imaging with different sets of stimulation parameters, a database may be constructed, such that the inverse problem of selecting parameters to match a particular brain region may be solved by consulting the database.

The individualized selection of parameters for the nerve stimulation protocol may based on trial and error in order to obtain a beneficial response without the sensation of skin pain or muscle twitches. Alternatively, the selection of parameter values may involve tuning as understood in control theory, as described below. It is understood that parameters may also be varied randomly in order to simulate normal physiological variability, thereby possibly inducing a beneficial response in the patient [Buchman T G. Nonlinear dynamics, complex systems, and the pathobiology of critical illness. Curr Opin Crit Care 10(5,2004):378-82].

Use of Control Theory Methods to Improve Treatment of Individual Patients

The vagus nerve stimulation may employ methods of control theory (e.g., feedback) in an attempt to compensate for motion of the stimulator relative to the vagus nerve and to avoid potentially dangerous situations such as excessive heart rate. Thus, with these methods, the parameters of the vagus nerve stimulation may be changed automatically, depending on environmental signals or on physiological measurements that are made, in attempt to maintain the values of the physiological signals within predetermined ranges.

When stimulating the vagus nerve, motion variability may often be attributable to the patient's breathing, which involves contraction and associated change in geometry of the sternocleidomastoid muscle that is situated close to the vagus nerve (identified as 65 in FIG. 8). Modulation of the stimulator amplitude to compensate for this variability may be accomplished by measuring the patient's respiratory phase, or more directly by measuring movement of the stimulator, then using controllers (e.g., PID controllers) that are known in the art of control theory, as now described.

FIG. 9 is a control theory representation of the disclosed vagus nerve stimulation methods. The "System" (patient) receives input from the "Environment." For example, the environment would include ambient temperature, light, and sound, all of which may be triggers of a migraine attack. If the "System" is defined to be only a particular physiological component of the patient, the "Environment" may also be considered to include physiological systems of the patient that are not included in the "System". Thus, if some physiological component can influence the behavior of another physiological component of the patient, but not vice versa, the former component could be part of the environment and the latter could be part of the system. On the other hand, if it is intended to control the former component to influence the latter component, then both components should be considered part of the "System."

The System also receives input from the "Controller", which in this case may comprise the vagus nerve stimulation device, as well as electronic components that may be used to select or set parameters for the stimulation protocol (amplitude, frequency, pulse width, burst number, etc.) or alert the patient as to the need to use or adjust the stimulator (i.e., an alarm). For example, the controller may comprise the control unit 330 in FIG. 1. Feedback in the schema shown in FIG. 9 is possible because physiological measurements of the System are made using sensors. Thus, the values of variables of the system that could be measured define the system's state ("the System Output"). As a practical matter, only some of those measurements are actually made, and they represent the "Sensed Physiological Input" to the Controller.

The preferred sensors will include ones ordinarily used for ambulatory monitoring. For example, the sensors may comprise those used in conventional Holter and bedside monitoring applications, for monitoring heart rate and variability, ECG, respiration depth and rate, core temperature, hydration, blood pressure, brain function, oxygenation, skin impedance, and skin temperature. The sensors may be embedded in garments or placed in sports wristwatches, as currently used in programs that monitor the physiological status of soldiers [G. A. SHAW, A. M. Siegel, G. Zogbi, and T. P. Opar. Warfighter physiological and environmental monitoring: a study for the U.S. Army Research Institute in Environmental Medicine and the Soldier Systems Center. MIT Lincoln Laboratory, Lexington Mass. Nov. 1, 2004, pp. 1-141]. The ECG sensors should be adapted to the automatic extraction and analysis of particular features of the ECG, for example, indices of P-wave morphology, as well as heart rate variability indices of parasympathetic and sympathetic tone. Measurement of respiration using noninvasive inductive plethysmography, mercury in silastic strain gauges or impedance pneumography is particularly advised, in order to account for the effects of respiration on the heart. A noninvasive accelerometer may also be included among the ambulatory sensors, in order to identify motion artifacts. An event marker may also be included in order for the patient to mark relevant circumstances and sensations.

For brain monitoring, the sensors may comprise ambulatory EEG sensors [CASSON A, Yates D, Smith S, Duncan J, Rodriguez-Villegas E. Wearable electroencephalography. What is it, why is it needed, and what does it entail? IEEE Eng Med Biol Mag. 29(3,2010):44-56] or optical topography systems for mapping prefrontal cortex activation [Atsumori H, Kiguchi M, Obata A, Sato H, Katura T, Funane T, Maki A. Development of wearable optical topography system for mapping the prefrontal cortex activation. Rev Sci Instrum. 2009 April; 80(4):043704]. Signal processing methods, comprising not only the application of conventional linear filters to the raw EEG data, but also the nearly real-time extraction of non-linear signal features from the data, may be considered to be a part of the EEG monitoring [D. Puthankattil SUBHA, Paul K. Joseph, Rajendra Acharya U, and Choo Min Lim. EEG signal analysis: A survey. J Med Syst 34(2010):195-212]. Such features would include EEG bands (e.g., delta, theta, alpha, beta).

Detection of the phase of respiration may be performed non-invasively by adhering a thermistor or thermocouple probe to the patient's cheek so as to position the probe at the nasal orifice. Strain gauge signals from belts strapped around the chest, as well as inductive plethysmography and impedance pneumography, are also used traditionally to non-invasively generate a signal that rises and falls as a function of the phase of respiration. Respiratory phase may also be inferred from movement of the sternocleidomastoid muscle that also causes movement of the vagus nerve stimulator during breathing, measured using accelerometers attached to the vagus nerve stimulator, as described below. After digitizing such signals, the phase of respiration may be determined using software such as "puka", which is part of PhysioToolkit, a large published library of open source software and user manuals that are used to process and display a wide range of physiological signals [GOLDBERGER A L, Amaral LAN, Glass L, Hausdorff J M, Ivanov P Ch, Mark R G, Mietus J E, Moody G B, Peng C K, Stanley H E. PhysioBank, PhysioToolkit, and PhysioNet: Components of a New Research Resource for Complex Physiologic Signals. Circulation 101(23,2000):e215-e220] available from PhysioNet, M.I.T. Room E25-505A, 77 Massachusetts Avenue, Cambridge, Mass. 02139]. In one embodiment of the present invention, the control unit 330 contains an analog-to-digital converter to receive such analog respiratory signals, and software for the analysis of the digitized respiratory waveform resides within the control unit 330. That software extracts turning points within the respiratory waveform, such as end-expiration and end-inspiration, and forecasts future turning-points, based upon the frequency with which waveforms from previous breaths match a partial waveform for the current breath. The control unit 330 then controls the impulse generator 310, for example, to stimulate the selected nerve only during a selected phase of respiration, such as all of inspiration or only the first second of inspiration, or only the expected middle half of inspiration. In other embodiments of the invention, the physiological or environmental signals are transmitted wirelessly to the controller, as shown in FIG. 5. Some such signals may be received by the docking station (e.g., ambient sound signals) and other may be received within the stimulator housing (e.g., motion signals).

It may be therapeutically advantageous to program the control unit 330 to control the impulse generator 310 in such a way as to temporally modulate stimulation by the electrodes, depending on the phase of the patient's respiration. In patent application JP2008/081479A, entitled Vagus nerve stimulation system, to YOSHIHOTO, a system is also described for keeping the heart rate within safe limits. When the heart rate is too high, that system stimulates a patient's vagus nerve, and when the heart rate is too low, that system tries to achieve stabilization of the heart rate by stimulating the heart itself, rather than use different parameters to stimulate the vagus nerve. In that disclosure, vagal stimulation uses an electrode, which is described as either a surface electrode applied to the body surface or an electrode introduced to the vicinity of the vagus nerve via a hypodermic needle. That disclosure is unrelated to the neurodevelopmental problems that are addressed here, but it does consider stimulation during particular phases of the respiratory cycle, for the following reason. Because the vagus nerve is near the phrenic nerve, Yoshihoto indicates that the phrenic nerve will sometimes be electrically stimulated along with the vagus nerve. The present applicants have not experienced this problem, so the problem may be one of a misplaced electrode. In any case, the phrenic nerve controls muscular movement of the diaphragm, so consequently, stimulation of the phrenic nerve causes the patient to hiccup or experience irregular movement of the diaphragm, or otherwise experience discomfort. To minimize the effects of irregular diaphragm movement, Yoshihoto's system is designed to stimulate the phrenic nerve (and possibly co-stimulate the vagus nerve) only during the inspiration phase of the respiratory cycle and not during expiration. Furthermore, the system is designed to gradually increase and then decrease the magnitude of the electrical stimulation during inspiration (notably amplitude and stimulus rate) so as to make stimulation of the phrenic nerve and diaphragm gradual.

Furthermore, as an option in the present invention, parameters of the stimulation may be modulated by the control unit 330 to control the impulse generator 310 in such a way as to temporally modulate stimulation by the electrodes, so as to achieve and maintain the heart rate within safe or desired limits. In that case, the parameters of the stimulation are individually raised or lowered in increments (power, frequency, etc.), and the effect as an increased, unchanged, or decreased heart rate is stored in the memory of the control unit 330. When the heart rate changes to a value outside the specified range, the control unit 330 automatically resets the parameters to values that had been recorded to produce a heart rate within that range, or if no heart rate within that range has yet been achieved, it increases or decreases parameter values in the direction that previously acquired data indicate would change the heart rate in the direction towards a heart rate in the desired range. Similarly, the arterial blood pressure is also recorded non-invasively in an embodiment of the invention, and as described above, the control unit 330 extracts the systolic, diastolic, and mean arterial blood pressure from the blood pressure waveform. The control unit 330 will then control the impulse generator 310 in such a way as to temporally modulate nerve stimulation by the electrodes, in such a way as to achieve and maintain the blood pressure within predetermined safe or desired limits, by the same method that was indicated above for the heart rate.

Let the measured output variables of the system in FIG. 8 be denoted by $y_i$ (i=1 to Q); let the desired (reference or setpoint) values of $y_i$ be denoted by $r_i$ and let the controller's input to the system consist of variables $u_j$ (j=1 to P). The objective is for a controller to select the input $u_j$ in such a way that the output variables (or a subset of them) closely follows the reference signals $r_i$, i.e., the control error $e_i=r_i-y_i$ is small, even if there is environmental input or noise to the system. Consider the error function $e_i=r_i-y_i$ to be the sensed physiological input to the controller in FIG. 8 (i.e., the reference signals are integral to the controller, which subtracts the measured system values from them to construct the control error signal). The controller will also receive a set of measured environmental signals $v_k$ (k=1 to R), which also act upon the system as shown in FIG. 8.

The functional form of the system's input u(t) is constrained to be as shown in FIGS. 2B and 2C. Ordinarily, a parameter that needs adjusting is the one associated with the amplitude of the signal shown in FIG. 2. As a first example of the use of feedback to control the system, consider the problem of adjusting the input u(t) from the vagus nerve stimulator (i.e., output from the controller) in order to compensate for motion artifacts.

Nerve activation is generally a function of the second spatial derivative of the extracellular potential along the nerve's axon, which would be changing as the position of the stimulator varies relative to the axon [F. RATTAY. The basic mechanism for the electrical stimulation of the nervous system. Neuroscience 89 (2, 1999):335-346]. Such motion artifact can be due to movement by the patient (e.g., neck movement) or movement within the patient (e.g. sternocleidomastoid muscle contraction associated with respiration), or it can be due to movement of the stimulator relative to the body (slippage or drift). Thus, one expects that because of such undesired or unavoidable motion, there will usually be some error (e=r−y) in the intended (r) versus actual (y) nerve stimulation amplitude that needs continuous adjustment.

Accelerometers can be used to detect all these types of movement, using for example, Model LSM330DL from STMicroelectronics, 750 Canyon Dr #300 Coppell, Tex. 75019. In one embodiment, one or more accelerometer is attached to the patient's neck, and one or more accelerometer is attached to the head(s) of the stimulator in the vicinity of where the stimulator contacts the patient. Because the temporally integrated outputs of the accelerometers provide a measurement of the current position of each accelerometer, the combined accelerometer outputs make it possible to measure any movement of the stimulator relative to the underlying tissue.

The location of the vagus nerve underlying the stimulator may be determined preliminarily by placing an ultrasound probe at the location where the center of the stimulator will be placed [KNAPPERTZ V A, Tegeler C H, Hardin S J, McKinney W M. Vagus nerve imaging with ultrasound: anatomic and in vivo validation. Otolaryngol Head Neck Surg 118(1,1998):82-5]. The ultrasound probe is configured to have the same shape as the stimulator, including the attachment of one or more accelerometer. As part of the preliminary protocol, the patient with accelerometers attached is then instructed or helped to perform neck movements, breathe deeply so as to contract the sternocleidomastoid muscle, and generally simulate possible motion that may accompany prolonged stimulation with the stimulator. This would include possible slippage or movement of the stimulator relative to an initial position on the patient's neck. While these movements are being performed, the accelerometers are acquiring position information, and the corresponding location of the vagus nerve is determined from the ultrasound image. With these preliminary data, it is then possible to infer the location of the vagus nerve relative to the stimulator, given only the accelerometer data during a stimulation session, by interpolating between the previously acquired vagus nerve position data as a function of accelerometer position data.

For any given position of the stimulator relative to the vagus nerve, it is also possible to infer the amplitude of the electric field that it produces in the vicinity of the vagus nerve. This is done by calculation or by measuring the electric field that is produced by the stimulator as a function of depth and position within a phantom that simulates the relevant bodily tissue [Francis Marion MOORE. Electrical Stimulation for pain suppression: mathematical and physical models. Thesis, School of Engineering, Cornell University, 2007; Bartosz SAWICKI, Robert Szmurlo, Przemyslaw Plonecki, Jacek Starzyński, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, 105 Press, 2008]. Thus, in order to compensate for movement, the controller may increase or decrease the amplitude of the output from the stimulator (u) in proportion to the inferred deviation of the amplitude of the electric field in the vicinity of the vagus nerve, relative to its desired value.

For present purposes, no distinction is made between a system output variable and a variable representing the state of the system. Then, a state-space representation, or model, of the system consists of a set of first order differential equations of the form d $y_i/dt=F_i(t,\{y_i\},\{u_j\},\{v_k\}; \{r_i\})$, where t is time and where in general, the rate of change of each variable $y_i$ is a function ($F_i$) of many other output variables as well as the input and environmental signals.

Classical control theory is concerned with situations in which the functional form of $F_i$ is as a linear combination of the state and input variables, but in which coefficients of the linear terms are not necessarily known in advance. In this linear case, the differential equations may be solved with linear transform (e.g., Laplace transform) methods, which convert the differential equations into algebraic equations for straightforward solution. Thus, for example, a single-input single-output system (dropping the subscripts on variables) may have input from a controller of the form:

$$u(t) = K_p e(t) + K_i \int_0^t e(\tau)d\tau + K_d \frac{de}{dt}$$

where the parameters for the controller are the proportional gain ($K_p$), the integral gain ($K_i$) and the derivative gain ($K_d$). This type of controller, which forms a controlling input signal with feedback using the error e=r−y, is known as a PID controller (proportional-integral-derivative). Commercial versions of PID controllers are available, and they are used in 90% of all control applications.

Optimal selection of the parameters of the controller could be through calculation, if the coefficients of the corresponding state differential equation were known in advance. However, they are ordinarily not known, so selection of the controller parameters (tuning) is accomplished by experiments in which the error e either is or is not used to form the system input (respectively, closed loop or open loop experiments). In an open loop experiment, the input is increased in a step (or random binary sequence of steps), and the system response is measured. In a closed loop experiment, the integral and derivative gains are set to zero, the proportional gain is increased until the system starts to oscillate, and the period of oscillation is measured. Depending on whether the experiment is open or closed loop, the selection of PID parameter values may then be selected according to rules that were described initially by Ziegler and Nichols. There are also many improved versions of tuning rules, including some that can be implemented automatically by the controller [LI, Y., Ang, K. H. and Chong, G. C. Y. Patents, software and hardware for PID control: an overview and analysis of the current art. IEEE Control Systems Magazine, 26 (1,2006): 42-54; Karl Johan Åström & Richard M. Murray. Feedback Systems: An Introduction for Scientists and Engineers. Princeton N.J.: Princeton University Press, 2008; Finn HAUGEN. Tuning of PID controllers (Chapter 10) In: Basic Dynamics and Control. 2009. ISBN 978-82-91748-13-9. TechTeach, Enggravhçgda 45, N-3711 Skien, Norway. http://techteach. no., pp. 129-155; Dingyu X U E, YangQuan Chen, Derek P. Atherton. PID controller design (Chapter 6), In: Linear Feedback Control: Analysis and Design with MATLAB. Society for Industrial and Applied Mathematics (SIAM).3600 Market Street, 6th Floor, Philadelphia, Pa. (2007), pp. 183-235; Jan JANTZEN, Tuning Of Fuzzy PID Controllers, Technical University of Denmark, report 98-H 871, Sep. 30, 1998].

The controller shown in FIG. 9 may also make use of feed-forward methods [Coleman BROSILOW, Babu Joseph. Feedforward Control (Chapter 9) In: Techniques of Model-Based Control. Upper Saddle River, N.J.: Prentice Hall PTR, 2002. pp, 221-240]. Thus, the controller in FIG. 9 may be a type of predictive controller, methods for which have been developed in other contexts as well, such as when a model of the system is used to calculate future outputs of the system, with the objective of choosing among possible inputs so as to optimize a criterion that is based on future values of the system's output variables.

A disclosure of the use of such feedback and feedforward methods to forecast and avert the onset of an imminent migraine attack was made in the co-pending, commonly assigned application U.S. Ser. No. 13/357,010 (publication US 2012/0185020), entitled Nerve stimulation methods for averting imminent onset or episode of a disease, to SIMON et al, which is incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for treating a medical condition in a patient, the method comprising:
positioning a device adjacent to, or in contact with, an outer skin surface of the patient, wherein the outer skin surface is adjacent to an auricular branch of the vagus nerve;
generating an electrical impulse sufficient to modulate a vagus nerve within the patient;
transmitting the electrical impulse transcutaneously through the outer skin surface to the vagus nerve such that the vagus nerve is modulated and thereby the medical condition is treated, wherein the electrical impulse comprises pulses having a frequency of about 2.5 kHz to about 7.5 kHz.

2. The method of claim 1, wherein the pulses have a frequency of about 5 kHz.

3. The method of claim 1, further comprising transmitting an electric current from the device through the outer skin surface to the vagus nerve.

4. The method of claim 1, wherein the electrical impulse is an electric field.

5. The method of claim 1, wherein the pulses have a pulse width of about 1 microsecond to about 1,000 microseconds.

6. The method of claim 4 further comprising varying the electric field to create burst periods and constant periods, wherein the charge of the electric field emitted during the burst periods alternates between positive and negative, wherein the frequency of the burst periods is about 1 to about 100 Hz.

7. The method of claim 1 further comprising positioning one or more electrodes near the outer skin surface and applying a voltage to the electrode(s) to generate the electric field.

8. The method of claim 6, wherein the charge of the electric field alternates between positive and negative 2 and 20 times per burst.

9. The method of claim 1, further comprising communicating data for one or more stimulation parameters wirelessly to the device.

10. The method of claim 9, further comprising communicating data from a remote source to a mobile device and wirelessly coupling the mobile device to the device in order to transmit the data to the device.

11. The method of claim 10, further comprising communicating authorization to the device in order to enable the device to operate.

12. A device for treating a medical condition in a patient, the device comprising:
a housing having a contact surface for contacting an outer skin surface of a patient adjacent to an auricular branch of the vagus nerve; and
an energy source coupled to the housing, the energy source being configured to generate an electrical impulse sufficient to modulate a vagus nerve within the patient and to transmit the electrical impulse transcutaneously through the outer skin surface to the vagus nerve such that the vagus nerve is modulated and thereby the medical condition is treated, wherein the electrical impulse comprises pulses having a frequency of about 2.5 kHz to about 7.5 kHz.

13. The device of claim 12 further comprising one or more electrodes coupled to the energy source, wherein the energy source applies a voltage to the electrode(s) to generate the electrical impulse.

14. The device of claim 12, wherein the energy source transmits an electric current through the outer skin surface to the vagus nerve.

15. The device of claim 12, wherein the pulses have a frequency of about 5 kHz.

16. The device of claim 12, wherein the electrical impulse is an electric field.

17. The device of claim 12, wherein the pulses have a pulse width of about 1 microsecond to about 1,000 microseconds.

18. The device of claim 16, wherein the energy source is configured to vary the electric field to create burst periods and constant periods, wherein the charge of the electric field emitted during the burst periods alternates between positive and negative, wherein the frequency of the burst periods is about 1 to about 100 Hz.

19. The device of claim 18, wherein the charge of the electric field alternates between positive and negative 2 and 20 times per burst.

20. The device of claim 12, wherein the energy source is housed within the housing.

21. The device of claim 12, further comprising a mobile device that receives data from a remote source, wherein the mobile device couples to the housing and transmits the data to the housing, wherein the data includes one or more stimulation parameters for treating a medical condition in the patient.

22. The device of claim 21, wherein the one or more stimulation parameters includes an amplitude of the electrical impulse.

23. The device of claim 12, wherein the energy source includes a signal generator within the housing.

* * * * *